United States Patent [19]
Tomich et al.

US005516890A

[11] Patent Number: 5,516,890
[45] Date of Patent: May 14, 1996

[54] BIOLOGICALLY MIMETIC SYNTHETIC ION CHANNEL TRANSDUCERS AND METHODS OF MAKING THE SAME

[75] Inventors: John Tomich, Pasadena; Mauricio Montal, La Jolla, both of Calif.

[73] Assignee: Synporin Technologies, Newport Beach, Calif.

[21] Appl. No.: 312,821

[22] Filed: Sep. 27, 1994

Related U.S. Application Data

[60] Division of Ser. No. 576,222, Aug. 31, 1990, Pat. No. 5,368,712, which is a continuation-in-part of Ser. No. 430,814, Nov. 2, 1989.

[51] Int. Cl.$^6$ .............................. A61K 38/04; C07K 7/00; C07K 5/00
[52] U.S. Cl. .................. 530/326; 530/327; 530/328; 530/329; 530/330; 530/331
[58] Field of Search ..................................... 530/326, 327, 530/328, 329, 330, 331; 514/13–18

[56] References Cited

PUBLICATIONS

Oiki, S. et al. (1988) M2 delta, a candidate for the structure lining the ionic channel of the nicotinic cholinergic receptor. *Proc. Natl. Acad. Sci.* USA 85, 8703–8707. See entire article; sequence of Torpedo AcChoR delta subunit in abstract and Fig. 1A Available to public Nov. 18, 1988.

Stewart, J. et al. "Solid Phase Peptide Synthesis", 2nd Ed. Pierce Chemical Co., Rockford, IL, 1984, see pp. 1–49.

*Primary Examiner*—Howard E. Schain
*Assistant Examiner*—Benet Prickril
*Attorney, Agent, or Firm*—Merchant, Gould, Smith, Edell, Welter & Schmidt

[57] ABSTRACT

The invention relates to synthetic proteins that can be used in in vitro sensing devices to detect the presence of physiologically active substances. The synthetic proteins are mimetic to native ion channels in mammalian systems. The invention also relates to a biosensor comprising a support assembly, a synthetic lipid bilayer containing the active channel protein. Lastly, the invention relates to the use of the biosensor disclosed in the application for the in vitro detection of physiologically active substances including antiseptics, antibiotics, neurotransmittors, and others.

4 Claims, 17 Drawing Sheets

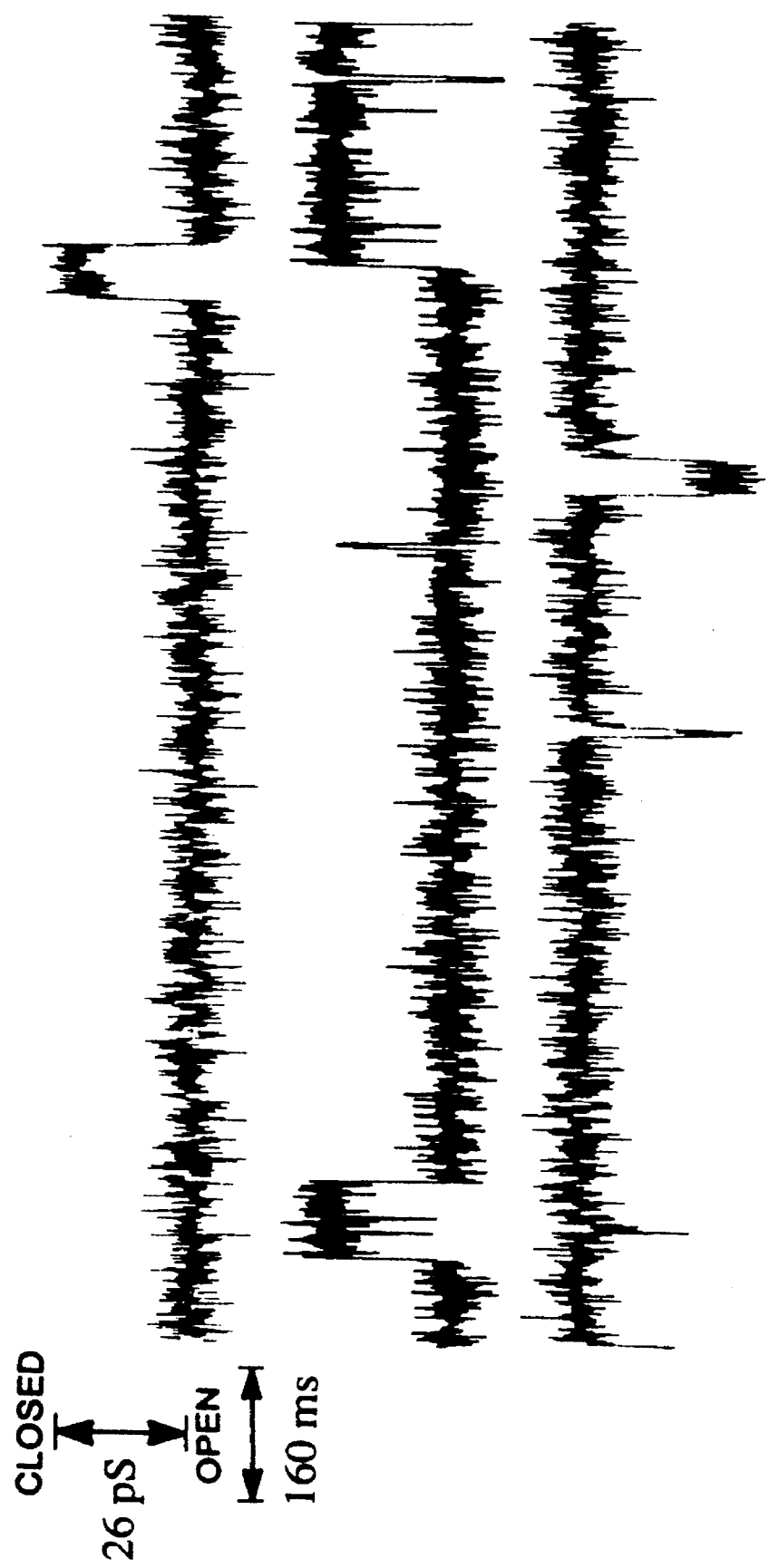

BIOLOGICALLY MIMETIC SYNTHETIC ION CHANNEL TRANSDUCERS AND METHODS OF MAKING THE SAME

CROSS REFERENCE TO RELATED APPLICATION

This application is a division of Ser. No. 08/576,222 filed Aug. 31, 1990, which issued as U.S. Pat. No. 5,368,712 on Nov. 29, 1994 and which was a continuation-in-part of application Ser. No. 07/430,814, filed Nov. 2, 1989, pending and entitled "SYNTHETIC ION CHANNELS AND BIOSENSOR" of John Tomich and Mauricio Montal.

FIELD OF THE INVENTION

The invention relates to methods of synthesizing polypeptides or protein which can function or ion channels. The invention also relates to systems, devices and methods for responding to, analyzing or detecting the physiological characteristics of physiologically active biological materials, and more particularly to such systems, devices and methods which use ion channels in a biosensor for the transduction of bioelectrical and biochemical events into measurable electrical signals.

BACKGROUND OF THE INVENTION

Ion channels in mammalian systems have been, and currently are, the subject of intensive scientific investigation because of the importance and variety of their biochemical functions. Ion channels are now understood to be polypeptide or protein structures with a tertiary-quaternary structure forming interior pores embedded in cell membrane walls, that can control the flow of ionic currents in response to either electrical excitation (voltage gating) or the presence of neurotransmitter (ligand gating). Current work shows that there are familial relationships or similarities in peptide sequence between the different types of voltage gated channels, such as those from mammalian brain, cardiac and skeletal muscles, including sodium, calcium, and potassium channels. Familial relationships within the ligand-gated types, such as acetylcholine receptors (AChR) (both neuronal and muscle), glycine receptors, and gamma aminobutyric acid (GABA) receptors also exist. More distant similarities also exist between these ion channels and ion channels derived from certain non-mammalian systems, studies of which have been instructive because of the accessibility of the proteins to analysis or the unique properties which the proteins exhibit. Research undertaken heretofore has initially concentrated on identifying the existence and general character and function of the channels. More recently it has broadened out greatly into detailed studies of the properties and interactions of specific ion channels, notably in electrical excitability and synaptic transmission with respect to the brain, heart and other muscle. This very important work has led to the development of a number of useful pharmaceuticals, such as the widely used channel blockers used to treat hypertension.

The functions of ion channel proteins have largely been studied by reconstituting the proteins from natural sources or replicating them by cloning techniques, and positioning them in a lipid bilayer membrane. The lipid bilayer duplicates the cell membrane to separate the aqueous ionic environment from the cell interior both physically and electrically while providing a support for the ion channel. The macromolecule forming the protein channel, positioned across the supporting lipid bilayer, can be coupled into a sensitive "patch clamp" circuit by which ionic current flowing through the channels can be precisely measured. The test procedures have been developed to the point at which "single channel" recordings can be made, so that the characteristics of individual "authentic" (or "native") channels can be studied. Using these techniques, the characteristics of many different ion channels have been precisely characterized from authentic, reconstituted, cloned and analog versions.

An ion channel does not simply open or close in response to a stimulus, but when activated functions in pulsed fashion or in what may be termed a relaxation mode. That is, it varies between open and closed states which last for intervals typically in the millisecond range. Furthermore, each type of ion generally exhibits a characteristic pattern of selectivity to different ions, and has a single channel conductance of predetermined amplitude under standard conditions. While reconstituted and expressed channel proteins can be generated for most types of ion channels they are often difficult and expensive to obtain, or unduly delicate, unstable and sensitive. Their use often gives rise to ambiguity when one seeks to alter or refine the protein chemistry. Efforts at protein synthesis of ion channels have heretofore sought to demonstrate ionic activity, but have not provided that degree of mimetic fidelity to the authentic channels that would permit meaningful use of the synthesized versions or assurance as to how improvements might be made. Examples are to be found in Oiki et al, *Proc. Natl. Acad. Sci. USA*, Vol. 85, April 1988, pp. 2393–2397, directed to the voltage-sensitive sodium channel, in Lear et al, *Science*, Vol. 240, (27 May 1988) pp. 1177–1181, and in Jullien et al, *Tetrahedron Lett.* 29, (1988) pp. 3803–3806. The Lear et al synthesis coupled protected helices to a solid support, and the helices were then cleared from the support. Further the protein ion channels were not intended to be mimetic, but were simply intended to show ionic permeability, being formed from repetitive sequences of two residues only Leucine for the apolar face of a helix and Serine for the polar face. The fact that an ion channel effect of higher fidelity to the authentic could be obtained was previously known, as evidenced by the Oiki et al reference, supra. In addition, it should be noted that Mutter et al, in *Tetrahedron*, 44:771–785 (1988) suggest that synthetic proteins may be made useful by linking amphipathic α-helix and β-sheet peptides to a tethering synthetic peptide template. This teaching does not, however, supply the deficiencies of the synthesized ion channel structures so as to render them mimetic of the authentic model.

If the kinetics and sensitivity of a synthetic ion channel do not correspond to the authentic channel, in an adequately mimetic way, then the synthetic channel is not useful to screen physiologically active substrates in a way useful to predict activity in human subjects. Non-mimetic proteins can be used only as a basis for further studies in molecular mechanics. To analyze a particular channel function in a meaningful way, or to screen chemicals to ascertain the precise nature of their pharmacological properties, a number of family-related synthetic ion channels are needed.

To achieve such results, however, major barriers must be overcome. The macromolecular structure of the sensing protein or transport site a channel protein cannot be exactly elucidated, as yet, using modern analytical instrumentation. The molecular structures are complex, and the exterior and interior geometries and encoding patterns which give rise to functional properties have not heretofore been fully understood and have not been predictable. Since the crucial functional attributes can only be measured indirectly, in electrical terms, the molecular dynamics are only partially understood or theoretically analyzed. The authentic voltage gated ion channel is believed to have an interior pore or aligning structure which enables ionic flow to take place, but that it also incorporates a sensor which is responsive to the triggering event and controls gating by some type of conformational change. The channels define a central-waterlike transmembrane pore or pathway of cylindrical shape with a converging lumen near the end. Internally, the macromolecule is regarded as having multiple subunits comprising α-helices of characteristic types. The active or gating portion of the channel is believed to comprise a chemically selective sensor for the ligand gated structure or electrically active adjacent helices forming ion pairs within the voltage gated structures. The ion channel must confine an aqueous solution Within the cell, must be fixed into the lipid membrane or onto a hydrolyzable peptide at its outer side, as well as insulate the active interior portions form the membrane. The pore cross-sectional dimension and cross-sectional area must also be compatible with the authentic channel. Further the synthesized peptides must fold into an energy minimized structure and in proper orientation to the membrane with hydrophilic and lipophilic sides in proper relation. Thus a substantial need exists for a synthetic protocol that can provide a single accurately mimetic synthetic channel protein. Further, the need to provide a generally applicable methodology to produce families of mimetics which is an even more complex problem remains unfulfilled.

The signal transducing properties of ion channels, their ability to provide net signal gain, their high sensitivity and their minimal size are a few of the factors which have led some to contemplate their use as biosensor. Examples are found in U.S. Pat. Nos. 4,637,861; 4,661,235; 4,776,944; 4,824,529 and 4,849,343, and also in Statutory Invention Registration H201. The ionic current characteristics of an ion channel are not functional unless it is embedded in, and provides a conductive pathway through, a dielectric or very high resistance (of the order of $10^{15}$ ohms) membrane, typically a lipid bilayer. Nonetheless the dominant and indispensable portion of this combination is the dynamic, event-responsive, ion channel. The referenced patents are however directed to the much simpler objective of stabilizing and strengthening a membrane. The production of active biosensor in the form of the instability, fragility and complexity of ion channels, rather than the characteristics of the membrane, is what has blocked the development of active biosensor of this class.

SUMMARY OF THE INVENTION

A biological transducer in accordance with the invention comprises a one or more single synthetic ion channel porin or an array of such porins embedded, in an active conformation and position, in a high resistive membrane. The porin or active polypeptide is characterized by a number of synthesized amphipathic polypeptides tethered at selected points to a polypeptide carrier or template protein. The polypeptides have an sequence ordered to form an active interior pore surfaces with surrounding molecular structures such that they have response characteristics mimetic to a chosen native channel even though the synthetic channel does not comprise the whole native channel but uses only selected subunits.

Methods of forming synthetic protein ion channels in accordance with the invention proceed from initial identification of likely subunit sequences in a native channel having amino acid sequences that are characterizable as candidates for controlling the gating function. Then one of a number of available protocols of polar and nonpolar residues is selected as a candidate for a self-folding unit of amphipathic properties having properly placed active sites. The individual α-helix design is refined for energy minimization and packing conformation and then from three to seven helices are assembled on a carrier template and embedded in a lipid bilayer. Thereafter, by testing responsiveness to standard excitation conditions, comparing to native channel responsiveness under the same conditions, and by targeted substitution of residues a final design is arrived at having a mimetic relation to the native channel.

The membrane and porin structures in a transducer are disposed as an electrically or chemically excited barrier in an aqueous ion environment incorporating means for measuring ionic currents through the barrier. Electrical or chemical excitation at the porin structure results in voltage or ligand gating of the ion current that is monitored and provides signal variations informative of the controlling agency. By using a family of such transducers of varying characteristics or by synthesizing variants on the transducers, or both, pharmacological properties of an unknown compound can be studied and analyzed in detail with realistic relation to an actual physiological response.

Faithful reproduction of authentic channel response characteristics is achieved by methodologies in accordance with the invention using synthetic porins that are substantially simpler than the native channel structures. Selected candidate structures are synthesized based upon a synthesized template or platform which is essentially planar. The template may form a U shape, enclosed shape or other configuration after tethering but which in any event has an open interior and a number of tethering points for attachment of polypeptide chains. The sequences are synthesized in essentially pure form by solid phase techniques to provide multiply folded transmembrane units which together define a synthetic porin having a lipophilic exterior for attachment to the membrane and a hydrophilic interior defining the channel lining and pore and providing compatibility with the aqueous ionic environment. However, the structure must usually be tailored by substitution or replacement of amino acid residues to have a measurable responsiveness corresponding to the authentic channel. This is accomplished by making single channel recordings under test conditions, and comparing these to the recordings of the authentic channels, then modifying the primary structure of the tethered polypeptides and the reactive sites until correspondence is achieved. There is thus provided a self-assembling, stable and robust protein channel that can be replicated whenever desired and in whatever quantity desired, and used for testing properties of pharmacological compounds or for the presence of particular compounds or characteristics.

Because these transducers are of macromolecular size and acutely sensitive to the presence of molecular agents, they provide a basis for measurement and analysis of trace amounts of specific compounds and families of compounds. Because high gain signal amplification techniques are available for measuring ion currents and because the single channel conductance, the ionic selectivity, the open and closed lifetimes, and the amplitudes of the ion currents all provide analog measurements, there is a basis for measurement of concentration as well as identification of the nature of the compound.

Voltage gated channels are understood to be characterized by the incorporation within the interior of the folded α-helical structure of oppositely charged ion pairs which undergo conformational change in response to the applied voltage. Ligand gated channels are understood to incorporate reactive sites responsive to the chosen agonists and antagonists and to undergo conformational change to affect ionic permeability of the porin in a comparable way to the native channels. The known characteristics of sodium channels of different origins, calcium channels and potassium channels in the voltage gated type, and AChR, GABA and glycine channels in the ligand gated type, provide potential models for synthesis.

One example of a porin transducer synthesized in accordance with the invention is provided by the acetylcholine receptor, the action of which controls synaptic transmission in the brain. This is based on the M2δ subunit of the native channel and a tetrameric, 23-mer residue sequence. Another example of a synthetic porin in accordance with the invention comprises the calcium channel from mammalian brain tissue. This is based on the 1VS3 subunit and a tetramer of 22-mer residues. Both have conductance, ionic selectivity and open and closed lifetimes mimetic of the native channel.

BRIEF DESCRIPTION OF THE DRAWINGS

A better understanding of the invention may be had by reference to the description herein, taken in conjunction with the accompanying drawings, in which.

DETAILED DESCRIPTION OF THE INVENTION

Figure 1:
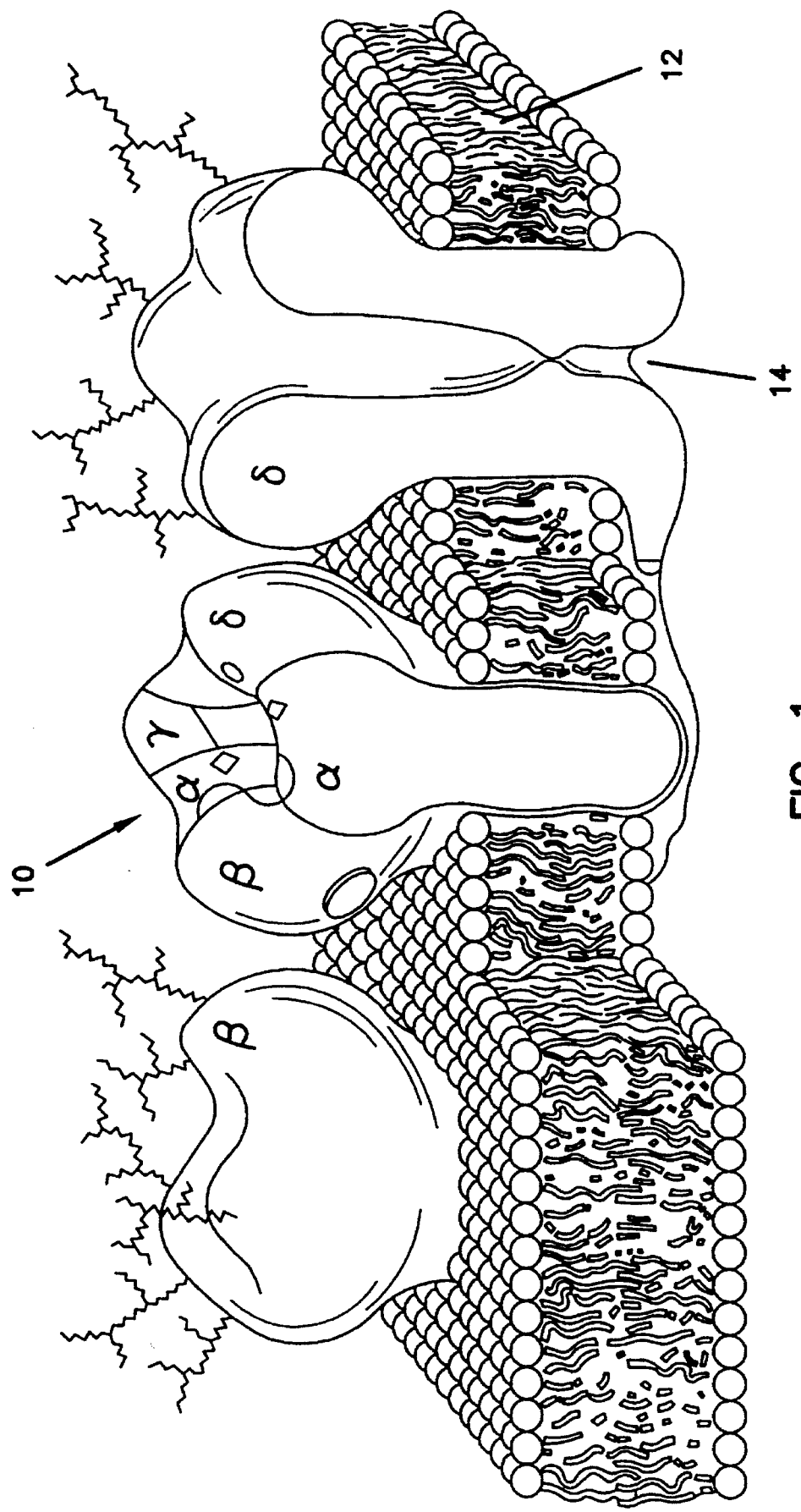
FIG. 1 is an idealized perspective view of a native ion channel structure embedded in a bilayer lipid membrane.

FIG. 1 depicts a conventional generalized representation of the geometry and disposition of a native ion channel 10 spanning a cell membrane 12, and including a central pore 14. The pore 14 provides an ion conductive pathway through the dielectric membrane 12 for the aqueous environment in the system. Although the pore 14 is of the order of a few to a hundred Angstroms in cross-sectional dimension, the gated ionic flow response through a single channel can be of sufficient magnitude to be monitored by the established voltage clamp technique.

The internal structure of the channel 10 body cannot be precisely investigated even by modern instrumentation. Thus the general conformation of FIG. 1 must be recognized as merely a representation of overall form. It is understood, from a multiplicity of studies of different ion channels, that they typically comprise a number of subunits. In the case of the acetylcholine receptor, as shown, there have been proposed to be five subunits, designated, $\alpha$, $\beta$, $\gamma$ and $\delta$, with the $\alpha$ unit being repeated twice. By site directed mutagenesis and cloning techniques it has been surmised that the $\alpha_1$ subunit plays a major role in channel gating. However, the influence of and interaction with other subunits, if any, largely remains to be determined, and existing techniques for modification and replication of specific structures do not afford assurance that other interactive effects have not been created.

Synthesis of purified protein structures for ion channel investigation has heretofore been attempted, as noted, in the sense that sequences of amino acid residues directed to a known active subunit have been formed. However, the mere existence of measurable ionic currents having conductance, ionic selectivity and open and closed lifetimes is only meaningful as a mark of progress. Unless a level of mimetic fidelity is attained which essentially corresponds to that of the native channel, the synthesized structure has no meaningful value as an indicator of biological response or an instrument for molecular analysis. Prior analyses of native ion channels and of synthesized protein channels lipid bilayers in other words afford certain potentials for further refinement, but have not established either a basic design protocol or a general methodology for synthesizing mimetics of the numerous forms of voltage and ligand gated channels.

Although there must be a profound appreciation of ion channel dynamics in the authentic channel, the problem of synthesis of a mimetic channel is much more complex because of the energetic, geometrical and compatibility requirements that must be satisfied in synthesizing a structure. Since the ion channel only has utility in a lipid bilayer membrane, synthesized channels must be stably formed and oriented in such a membrane and have a pore that spans the membrane and have a cross-sectional dimension and area corresponding to the native model. For energetic and density reasons, the peptide chains must fold into compact helices. In so folding, a number of specific rules must be observed. The helical chains/sequences must be amphiphilic, with hydrophilic residues facing the interior of the pore and lipophilic residues at the membrane. Other hydrophilic and neutral residues are largely confined to the interior of the structure, with charged residues at the interior for participation in the ionic flow control phenomenon. Signal transduction events in the presence of voltage or ligand energizing factors must thereafter correspond to the authentic channel. Applicants' studies show, as described in more detail hereafter, that depending upon the channel there are certain residues which must also be appropriately placed and positioned to control the characteristic gating action in the manner desired.

SYNTHESIZED ION CHANNEL PROTEIN CONCEPTS

Figure 2:
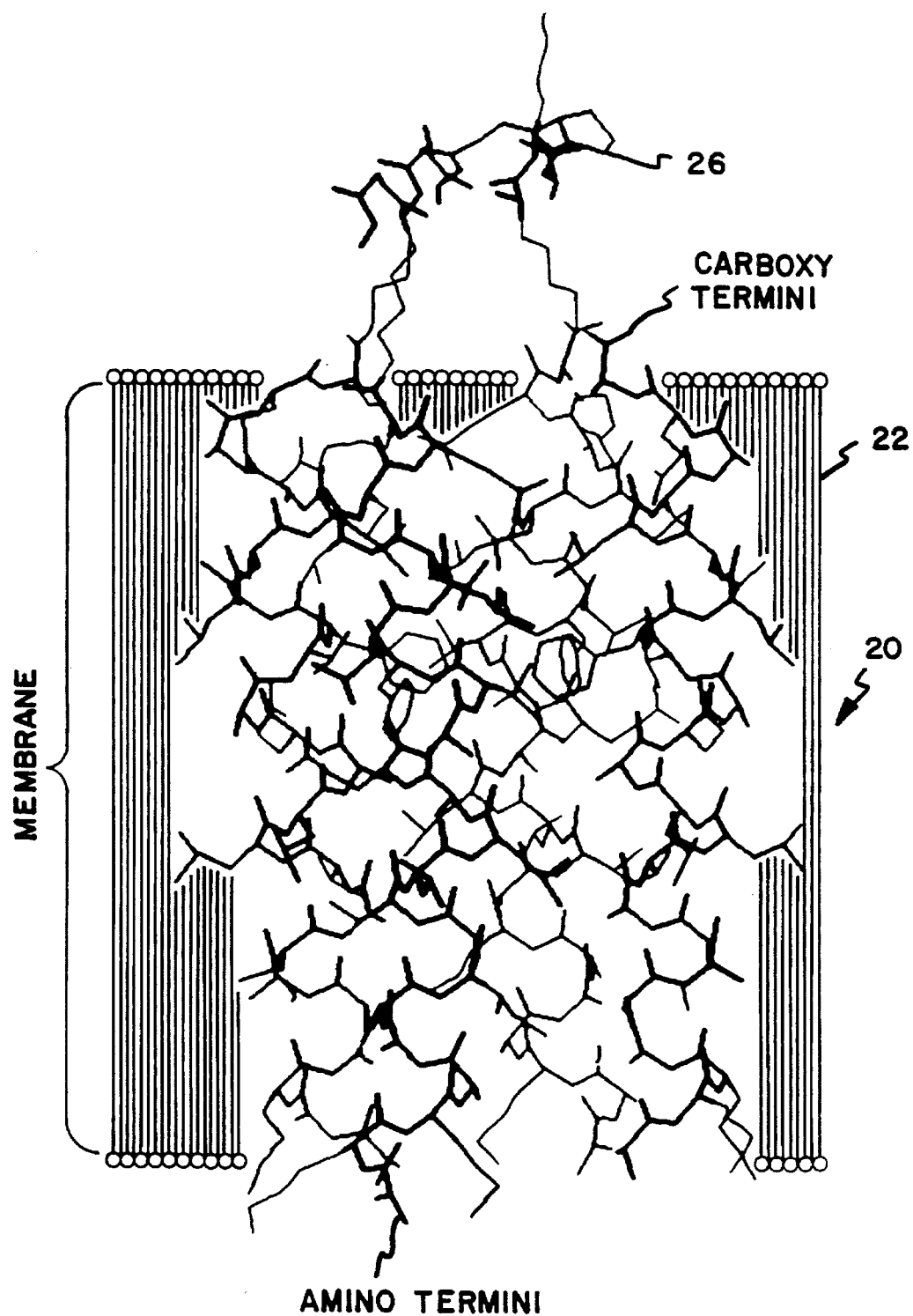
FIG. 2 is an idealized side view depiction of a synthetic porin shown as a computer generated molecular model of an AChR channel including a number of oligopeptides tethered to a synthetic multifunctional carrier template and within a bilayer lipid membrane.
Figure 3:
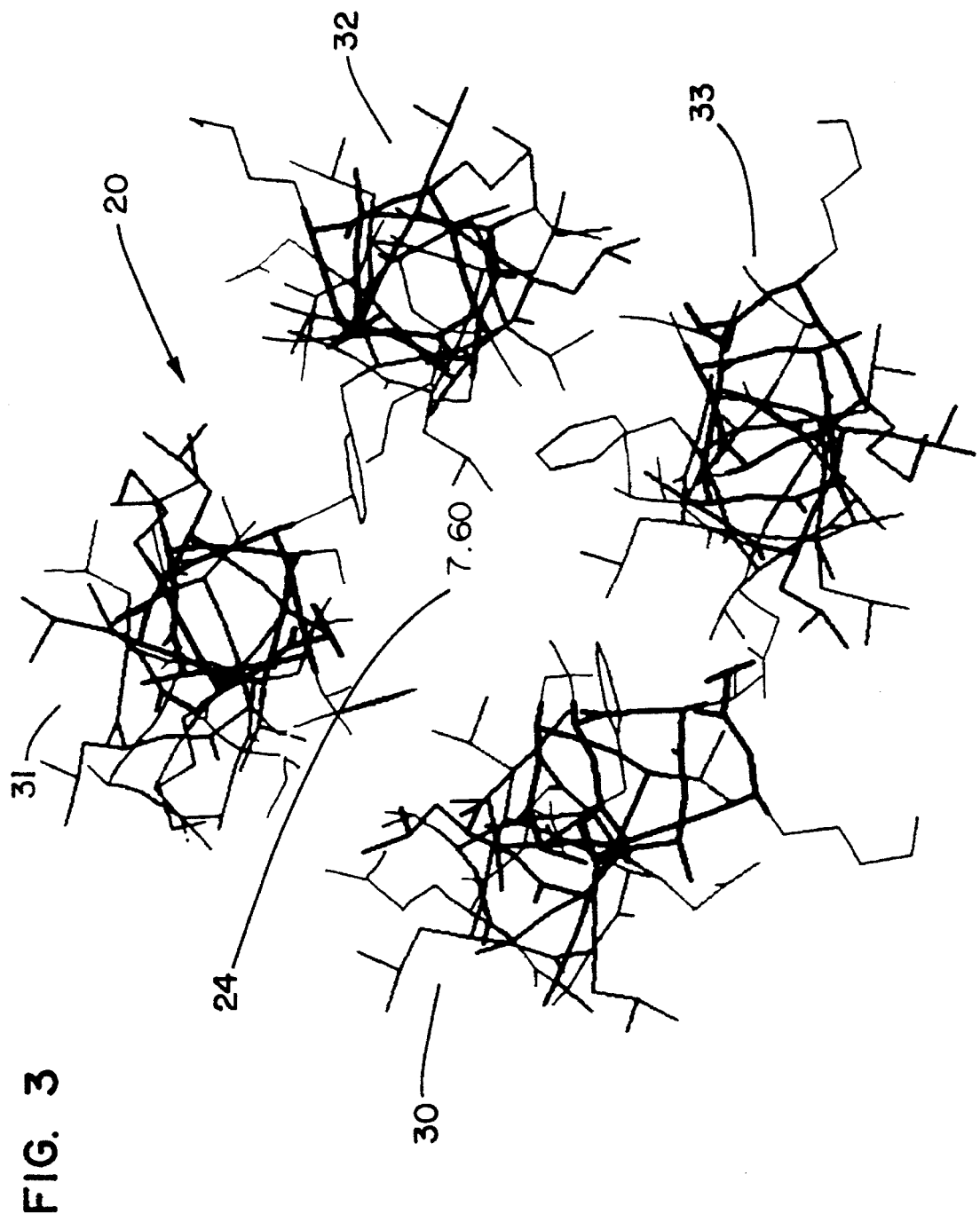
FIG. 3 is an end view of the synthetic porin of FIG. 2.

Protocols and methods in accordance with the invention, referring now to FIGS. 2 and 3, derive a synthesized protein channel structure 20 here exemplified as the AChR channel in computer generated form. The synthetic porin 20 is embedded in and spans a bilayer lipid membrane 22, and exposed to an ionic aqueous environment that extends into the pore 24 (FIG. 3). The channel structure 20 also comprises a synthesized multi-residue, internally open sequence of amino acids which may here be characterized as of U-shape, and which forms a template or backbone 26 best seen in FIG. 2 to which synthetic transmembrane protein arrays are tethered. The template 26 may alternatively form other outlines, such as a closed ring. A template structure may be provided at one or both ends of the channel 20, but must include the central opening permitting ionic passage. To form the pore and body of the channel 20, oligopeptides 30, 31, 32 and 33 (FIG. 3) having selected residue sequences are tethered to selected junction points on the template 26 and span the membrane, which has a thickness of 30–35A. Although four peptides are shown in the example, the number may vary from a minimum of three to a maximum of seven, for different synthesized channels as described hereafter.

The four helix bundles 30, 31, 32, 33 have carboxy termini joined to lysine side chains extending from the template 26 at the tethering points, and have amino termini at the opposite cytoplasmic side of the membrane. Side chains from the amino acid residues are not visible in this image, but seal the central aqueous pore 24. The amino termini comprise glutamic acid having negative charge that enrich the pore with counterions ($Na^+$ or $K^+$) which are the electric current carriers. The pore forming segments include serine —OH side chains exposed at the channel pore lining, and participate in the passage of hydrated ions. The central region of the pore thus defined is substantially void of charge since the charged residues are principally at the ends of the transmembrane helices.

The template 26 is generally synthesized first, in which event the tethering sites must be protected during processing until assembly is complete, when they are deprotected to form reactive sites for attachment of the polypeptides. Alternatively, the chain of residues making up the template 26 may be serially assembled, with each tethered oligopeptide being attached after each associated template tether residue is added to the growing template polypeptide.

FIG. 4 depicts, again in computer synthesized form a synthesized calcium channel 40 tethered to a template 42 of the form previously illustrated. In this example the backbones of the four separate helices 44, 45, 46, 47 are graphically depicted, and show more graphically the relative positions of the helices. They also show, as can be seen. somewhat in FIG. 3, the characteristic tilt of the helices of about 20° to 30° relative to an axis normal to the membrane surface. In the calcium channel, aspartic acid residues having negative charges present side chains in the channel lining near the amino termini to enrich the entry of the channel with cations. Side chains of negatively charges aspartate and glutamate residues form part of the interior channel lining to select positively charged calcium ions during transmembrane flow.

Figure 4:
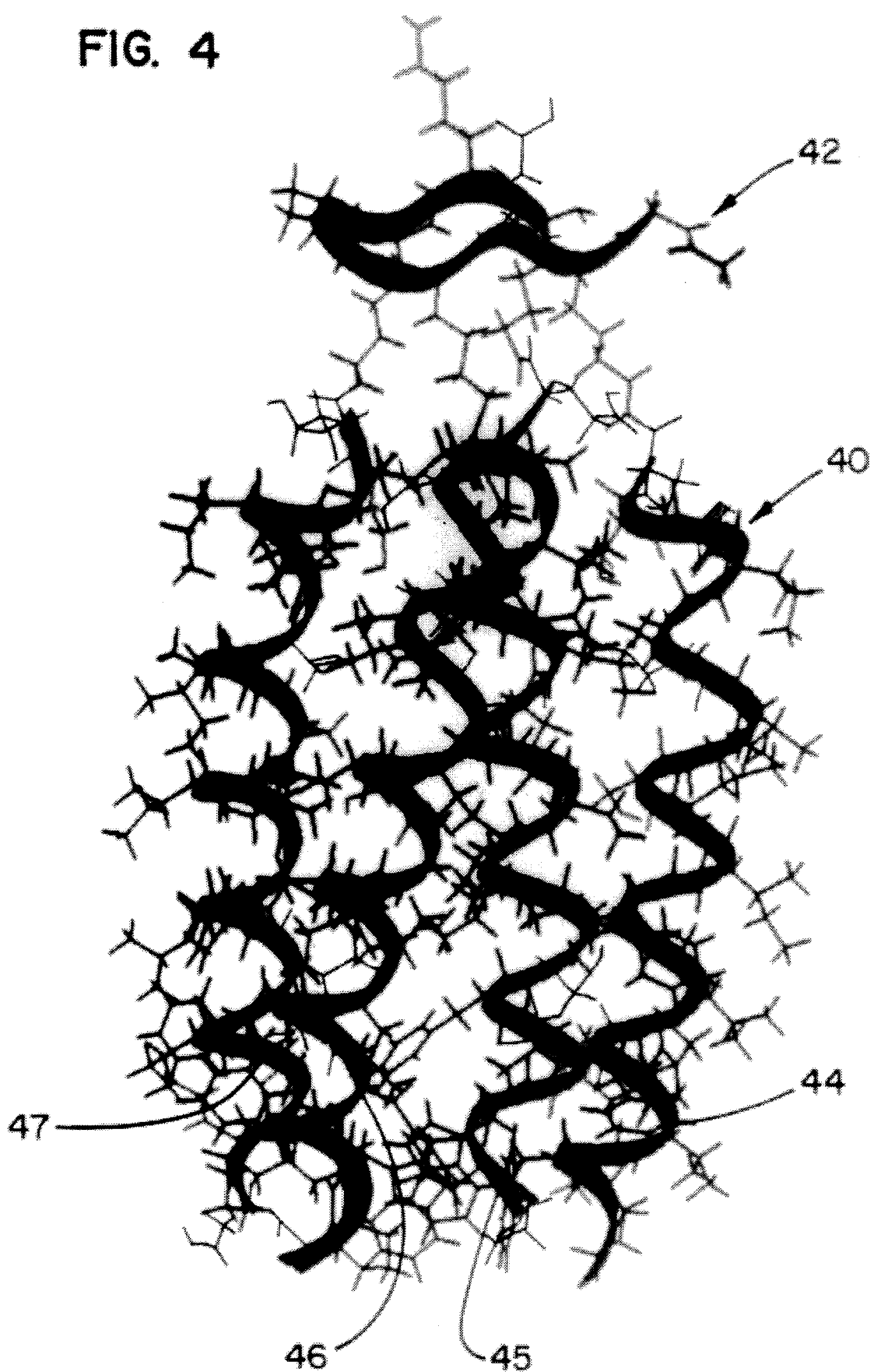
FIG. 4 is an idealized side view of a synthetic porin represented by a computer generated molecular model of a calcium channel, the bilayer lipid membrane.
Figure 5:
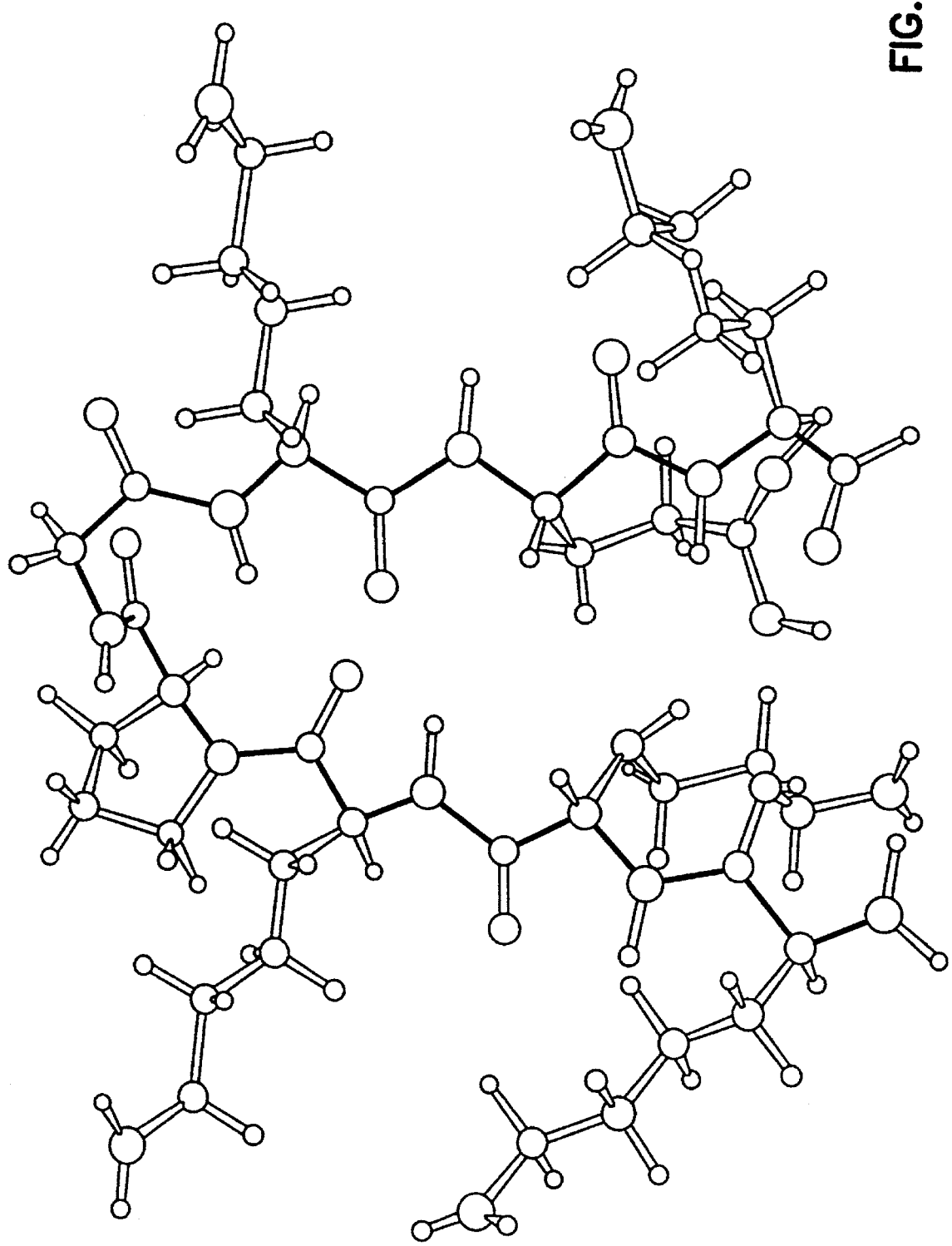
FIG. 5 is an idealized top view of a synthetic template (with bold bonding) in computer generated form.

The template 26 chosen for the examples of FIG. 2–4 is shown in idealized form in FIG. 5. This is a nine residue structure including the sequence $K^{R1}$, $KK^{R2}$, $PGK^{R3}$, $EK^{R4}$, having four tethering points (R1 to R4) with lysine side chains for attachment of the peptides.

Figure 6:
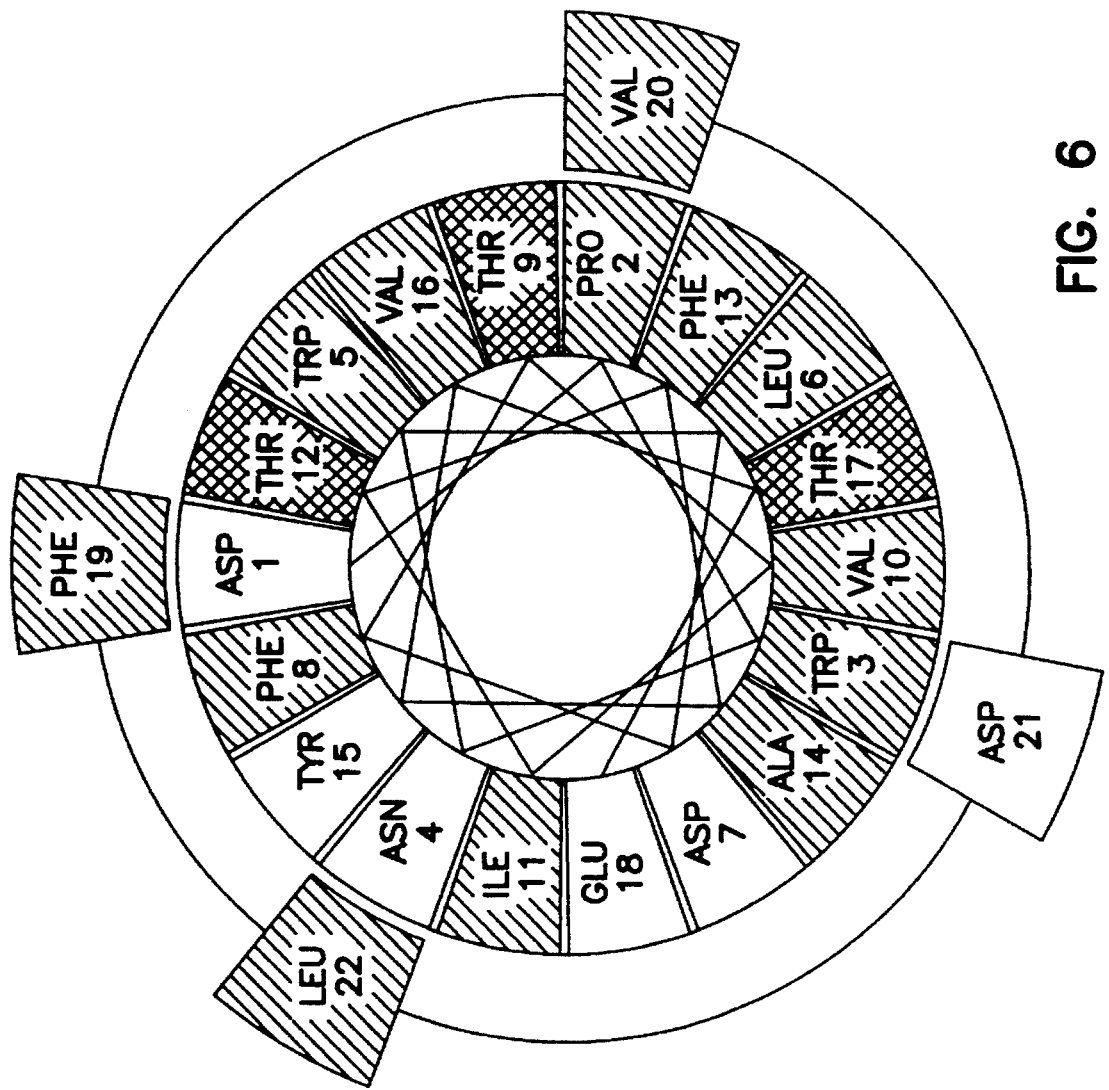
FIG. 6 is a helical wheel representation of the distribution of amino acid residues in an exemplary ion channel structure in accordance with the invention.

The polypeptide chains must be sufficiently long to traverse the thickness of the membrane 22, and this ordinarily requires a 22-mer or 23-mer sequence. This exceeds the minimum length thought to be necessary for self-folding, which is thought to be in the range of 11 to 15 residues for different sequences. The peptide sequence is determinative of the conformation to be assumed. It is essential that each helically folded body in the tetramer have an amphipathic structure such that within the tetramer those outer sides adhering to the membrane 22 are lipophilic and those sides exposed at the pore interior are hydrophilic. Internal residues will predominantly be hydrophilic neutral. This is shown more clearly in the helical wheel representation of FIG. 6, showing one helix of a calcium channel with hydrophilic residue shared. The internal faces of the pores must moreover provide sites for the functional gating elements of the channel, whether of the ligand gated or voltage gated type. When these requirements are met the channel structure 20 inserts into the membrane 22, defining the requisite interior pore that is compatible with the aqueous ionic environment.

Thus, even though the complex multi-unit native channel is not replicated in its different subunits, and the polypeptides comprise repetitions of one subunit or portion thereof only in some examples, there is mimetic fidelity in terms of ionic response characteristics to physiologically active substances and potential diffusion, and there are the sole measurable transducer properties.

The protocols to be followed in assembling amphipathic α helices require as preconditions that the oligomeric number be high enough to enable folding to take place, and to provide a length sufficient to span the membrane. We have established, moreover, that the protocols also typically require observance of one of the following sequence periodicities in polar (P) and nonpolar (N) residues in order to have the needed amphipathic characteristic:
1. (PNNN)5
2. (PNNN PNN)3
3. (PPNN PNN)3

The polar (P) residues can comprise Serine (S), Threonine (T), Aspartate (D) or Asparagine (N), Glutamate (E) or Glutamine (Q), and Histidine (H), while the nonpolar (N) residues can comprise Leucine (L), Isoleucine (I), Valine (V) and Alanine (A). A self assembled folded peptide incorporating such sequences, however, has without more a very low statistical probability of functioning with fidelity as a mimetic of a native channel. The selection must be based on knowledge of the native channel protein sufficient to identify geometrical and chemical characteristics of the pore structure to be simulated. Precise or exact identification is not needed at the outset because of substitutions and alterations that are feasible in the synthesis approach. Certainty in fact cannot be obtained by analysis of authentic channels using presently available instruments and techniques. However, by identifying the internal structure of a reconstituted or expressed channel within the constraints imposed by the present level of knowledge, a satisfactory unifying structural motif can usually be postulated.

A methodology for deriving models for plausible channel structures for both voltage-gated and ligand-regulated channel proteins is given by M. Montal in Chapter 1 "Channel Protein Engineering," pp. 1–31 of the book *Ion Channels, Vol. 2*, edited by T. Narahashi, Plenum Publishing. Corp. (1990), which is only summarized herein and the full contents of which are incorporated by reference. By study of the primary structure of a channel protein, inferences are derived as to the protein interior and as to the pore structure and the ion-channel forming domain. In the voltage-gated channels a high degree of homology conservation is noted in amino acid sequences, justifying, after one channel protein is synthesized the assumption that a series of other amphipathic α-helices can be formed that have sufficient length to traverse the membrane and define an appropriate pore size for other channels. Secondary structure predictors and helical wheel representations (as in FIG. 6) are used to postulate the existence of the helical form, potential hydrophilic and hydrophobic regions, to determine residue location on the helix and to propose beneficial sequence alternatives. Using known computer analysis techniques for energy minimization, a stable, low-energy conformation is found in which the interior has an excess of negative charged residues forming a cation pathway and acidic residues located in the channel lining determine channel selectivity.

Similar design approaches for ligand-regulated channels assure the desired amphipathic structure in energy-minimized form, with binding residues desirably placed in the lumen of the pore. The structural motif will also typically demonstrate sufficient evolutionary conservation among species, and sufficient tolerance to amino acid substitution, to reduce the complexity of the design problem. Bowie et al, in the article "Deciphering the Message in Protein Sequences: Tolerance to Amino Acid Substitutions," *Science*, Vol. 247, Mar. 16, 1990, pp. 1306–1310, have asserted that there is surprising tolerance and that this confirms findings of others that many positions are phenotypically silent. Therefore, a suitably profound understanding of the native channel model enables application of the design protocol and predictive rules with reasonable expectation that the template assisted, polypeptide structure will function as an ion channel that can at least serve as the basis for a mimetic adaptation.

A particular example of interest is presented by the nicotinic acetylcholine receptor (AChR), the structure and properties of which were studied at length, as in Chapter 8, "The Reconstituted Acetylcholine Receptor", pp. 157–203 of the book *Ion Channel Reconstitution*, edited by C. Miller, and published by Plenum Publishing Corp. (1986). This article shows (p. 158) the structural model of FIG. 1, including the pentameric $\alpha_2 \beta \gamma \delta$ complex, and the amino acid sequences. Understanding at that time of the molecular events underlying the opening of the postsynaptic channel did not permit clear identification of the subunit or subunits or portion thereof critical to channel-gating kinetics. However, the subsequent article by Oiki et al, supra, led to the suggestion, p. 8703, that the lining of the ionic channel might comprise five amphipathic α-helices. Further it is shown below in detail that a 23-mer peptide assembly of four parallel units tethered on a template to replicate the M2δ segment exhibited conductances, ionic selectivity open channel lifetimes, and sensitivity to anesthetic channel blockers characteristic of the authentic channel, when embedded in a lipid bilayer membrane.

Another example of interest (the sequence used) is described more specifically below (in example relating to the $Ca^{++}$ channel sequence) is directed to the synthesis of a dihydropyridine-sensitive calcium channel from skeletal tissue. Based upon cloned and sequenced protein components, as reported by T. Tanabe et al, *Nature* 328, (1987) pp. 313–318 a primary structure was postulated having four internal repeats, each with six presumably α-helical transmembrane segments. Again tethering the polypeptides to different points on a carrier template, a synthetic protein in ion-channel geometry was formed using four identical 22-mer peptides each corresponding to the transmembrane segment 1VS3. The synthetic channel formed cation-selective channels in lipid bilayers, with single channel conductances in different ionic media, and with blocking responses to specific anesthetics, mimetic of the authentic channel. This approach not only verifies, by the observed ionic properties, the assumptions as to the deduced primary structure, but also identifies the active portion of the pore-forming structure. It is to be noted that useful work on the skeletal muscle calcium channel, based upon polyclonal methodology, has left uncertain the question of which subunits are required for a native functional channel. This work is described by S.D. Jay et al in the article "Primary Structure of the γ Subunit of the DHP—Sensitive Calcium Channel from Skeletal Muscle," *Science*, Vol. 148 (Apr. 27, 1990) pp. 490, 491. They state that it is "unknown which subunits are required for a native functional DHP-sensitive $Ca^{2+}$ channel," and conclude that the "channel activity may be a result of a multi-subunit complex containing" the four subunits $\alpha_1$ $\alpha_2$ β and γ. Further they surmised that while an expression of the $\alpha_1$ subunit in tissue culture cells was previously able to produce DHP-sensitive current but with much slower activation than in the native tissue, the γ subunit might contribute to channel activation, and that further "channel activity may be the result of a multi-subunit complex" containing the four subunits. Jay et al recognize that the "$\alpha_1$ subunit, with 24 putative membrane-spanning segments, is the principal transmembrane subunit of the complex and has significant sequence homology with several other members of the voltage dependent ion channel family."

Applicants show herein, however, that a synthetic protein which is structurally based on a carrier template can be assembled with a number of peptides arrayed to form a stable, folded configuration which defines synthetic pores. Moreover active binding sites in the pore function with properties mimetic of the authentic channel. Furthermore, the same methodology serves for developing variants within a family of channels.

The validity of this approach is further confirmed by its potential for synthesizing template-based channel proteins for other voltage sensitive protein channels, including putative potassium channels from the Shaker locus of Drosophila and mammalian brain, and for ligand-gated channel proteins from the brain, including γ-aminobutyric acid (GABA) receptor (E) and the glycine receptor. In addition to inferences which can be drawn as to certain subunits, there are also a number of conserved residues and specific distinct features which can be accounted for in synthesis. However it can be considered that superfamilies of voltage-gated and ligand-regulated channels exist and facilitate protein channel design and fabrication with controlled folding, assembly and compaction.

The gating function is realized in synthetic porins in accordance with the invention even though the present levels of instrumentation and understanding do not afford a definitive view of how the function is carried out internally to the porin or how function is specifically related to structure. Given that helices are tethered in parallel or anti-parallel relationship, several hypothesis exist to explain the opening and closing of the pore, all based upon some differential translation of the helices, or parts thereof. One hypothesis is that the helices respond to the sensed condition by rotation about their transmembrane axis so as to gate the pore in response to the functioning of the sensor function. Another hypothesis is that the anti-parallel helical pair structure of the voltage sensing element in the voltage sensitive change undertakes differential translation, in response to applied voltage, in the direction normal to the membrane surface. Yet another hypothesis is that there is both change of interhelical tilt and differential translation in the conformational change which closes the channel. Whatever the specific nature of the gating action, it must be borne in mind that gating, self folding and helical compatibility are not met automatically by the selection of a plausible sensor sequence.

The helical oligomers tethered to a common template in the exemplary synthetic porins are in parallel relationship, with their carboxy termini attached to the template and amino termini at the untethered end. In the so-called anti-parallel geometry the oligomers lie substantially parallel to the same axis, but in alternating head to tail relationship. Anti-parallel structures are considered to exist, for example, in the internal portions of at least some voltage-gated ion channels, so as to define sensor structures comprising a helical pair of a positively charged helix and a negatively charged helix. The anti-parallel helical pair structure also satisfies other structural and energetic requirements of the voltage sensing element in terms of a hydrophobic exterior and a highly charged interior, and the formation of voltage-sensitive depolar clusters. These considerations lead to the likely conclusion that applied electric fields disrupt the interior ion pairs and rearrange the helices to effect channel opening (activation) and deactivation. Because anti-parallel helical structures have different stability than parallel structures, and because a degree of instability is required to allow conformational changes, this difference can be of benefit in the design of a synthetic channel.

IOMC Conduction, Slectivity and Channel Gating Kinetics

Figure 7:
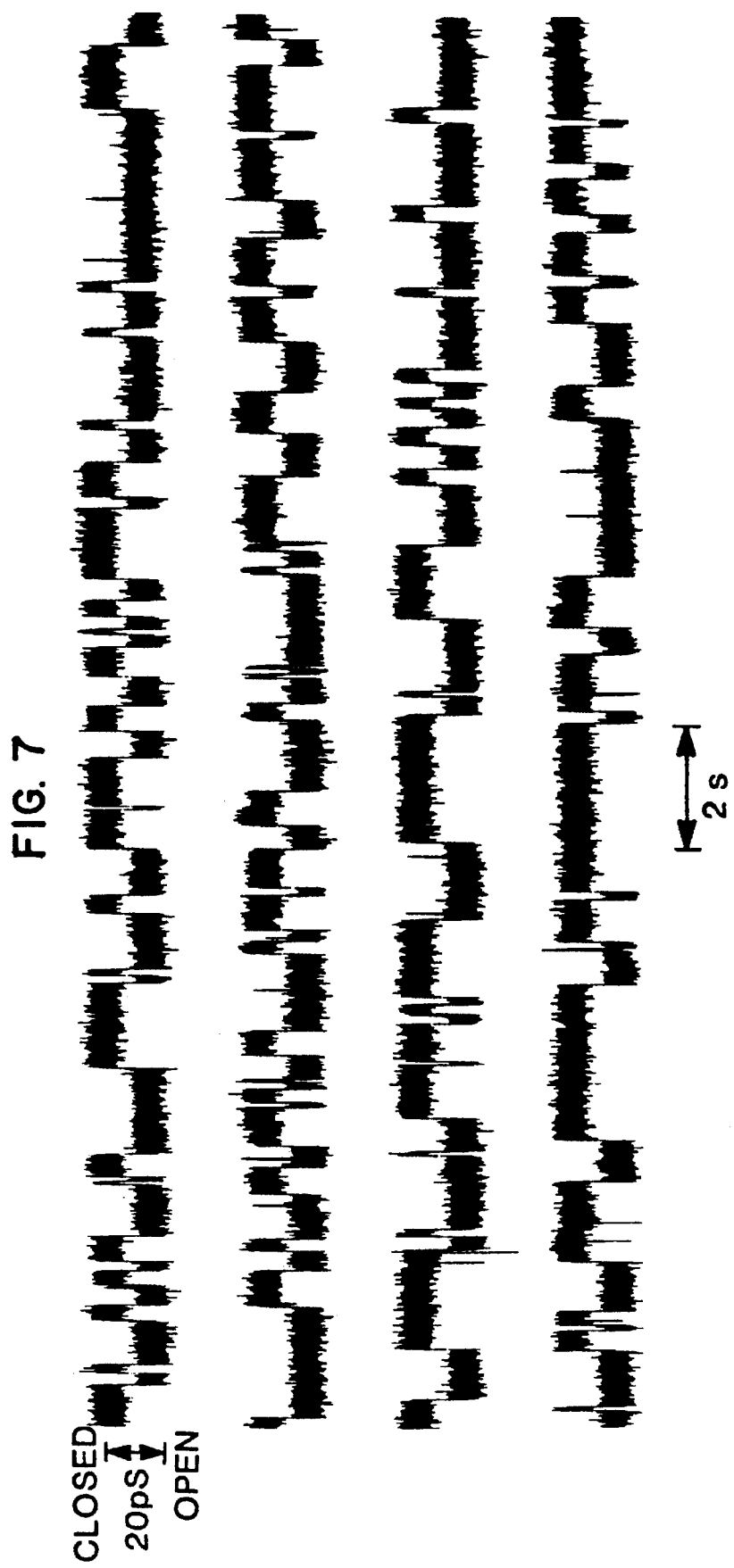
FIG. 7 comprises a series of ionic conduction waveforms taken from single channel recordings of tethered tetrameric M2δ proteins in bilayer lipid membrane.
Figure 8:
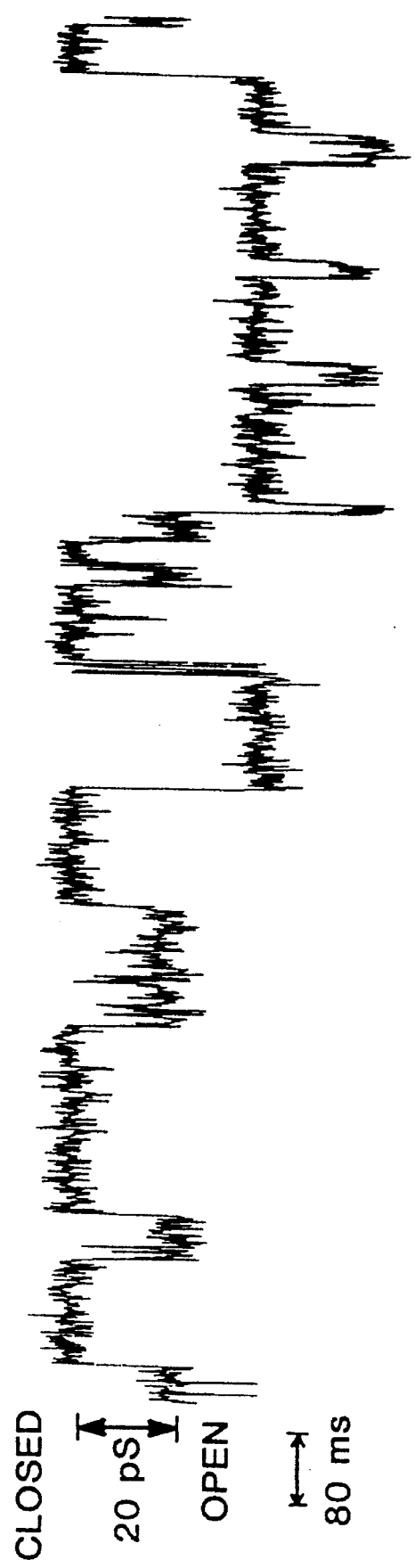
FIG. 8 comprises a waveform of ionic conduction characteristics taken from single channel recordings of M2δ synthetic porins.

Using established recording, filtering, digitizing and data processing techniques, single channel recording were made of single channel recordings for tethered tetrameric M2δ proteins and free M2δ proteins (FIGS. 7 and 8 respectively). Conductance (V) and lifetime (T) values were determined from a multiplicity of events, and single channel open and closed lifetimes were discriminated using a published pattern recognition algorithm.

As seen from FIG. 7, representing currents flowing through single channel tethered M2δ proteins, there are distinct open and closed states. There is homogeneity in the unitary conductance events and the open states frequently last several seconds. Consequently it can be said that this structure clearly forms ionic channels in lipid bilayers. These recordings were made in symmetric 0.5M KCl (pH 7.4) and recorded at 100 mV. In control, as FIG. 8 shows, free (monomeric) M2δ forms channels of heterogenous amplitudes and open lifetimes, with clearly discernible distinct events in which V=20 pS (pico Siemens) and V=40 pS. These were recorded at 0.5M NaCl (pH 7.2) and 100 mV.

A number of reversal potential measurements were made with channels in bilayers, under single salt gradients of KCl or NaCl. With 10 fold salt gradients (0.5M–0.05M) and current voltage (I-V) measurements between −100 mV and 100 mV, the I-V relations were practically linear. Calculation of transference numbers from reversal potential measurements indicated No. 4 that the pore is cation selective with values>0.96+0.03 (N–6).

Also, the residence times of the tethered M2δ synthetic porin in the open state range, as seen in FIG. 2, from the millisecond to the second time scale. Fitting the open and closed lifetimes ($T_c$ and $T_c$ respectively) with the sum of two exponentials (a conventional and published analytical approach) for symmetric 0.5M KCl and 0.5M NaCl solutions, the time constants were as follows for the fitted curves:

$T_{o1}$=0.62+0.31 MS;=0.9+0.5 MS $T_{o2}$=67.4+31 MS;=25.4+15 MS $T_{c1}$=2.7+2.1 MS;=1.2+0.5 MS $T_{c2}$=294.1+100 MS (N=15); $T_{c2}$=7 MS (N=4)

Comparing these analytical results to published literature for authentic AChR channels, the tethered M2δ tetramer forms ionic channels in lipid membranes with similar single-channel properties (V, cation selectivity and kinetics of transition between closed and open states).

Figure 9A:
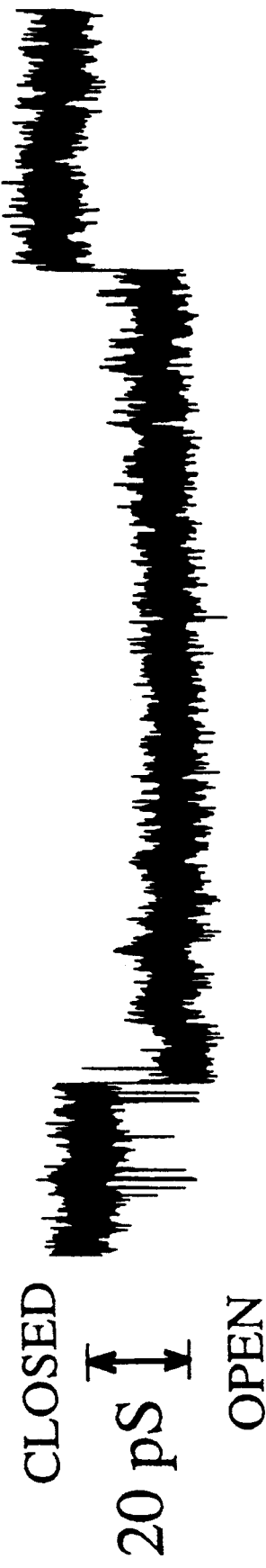
FIG. 9 comprises waveforms (A) and (B) recorded before and after, respectively, exposure of the tethered M2δ porins to a blocking local anesthetic.
Figure 9B:
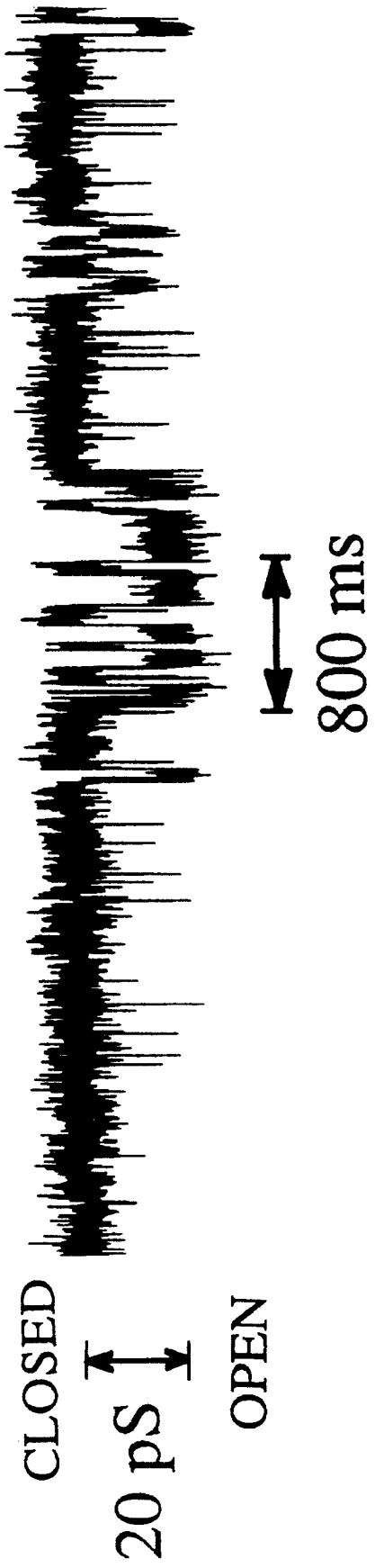

Furthermore, the pharmacological specificity of the pure structure generated by the tetrameric M2δ synthetic porin was examined by using a quaternary derivative (QX-222) of the local anaesthetic lidocaine. QX-222 is known to transiently block the flow of current through the AChR channel, thereby reducing the channel open lifetime. FIGS. 9A and 9E show comparative single channel recordings of this synthetic porin before (FIG. 9A) and after (FIG. 9B) addition of 25 μM QX-222. The result is that the characteristic brief and long open lifetimes exist prior to application of the anaesthetic, as previously shown in FIG. 7. In the presence of QX-222 the channel open time is drastically shortened even though V is virutally unaffected.

Figure 10B:
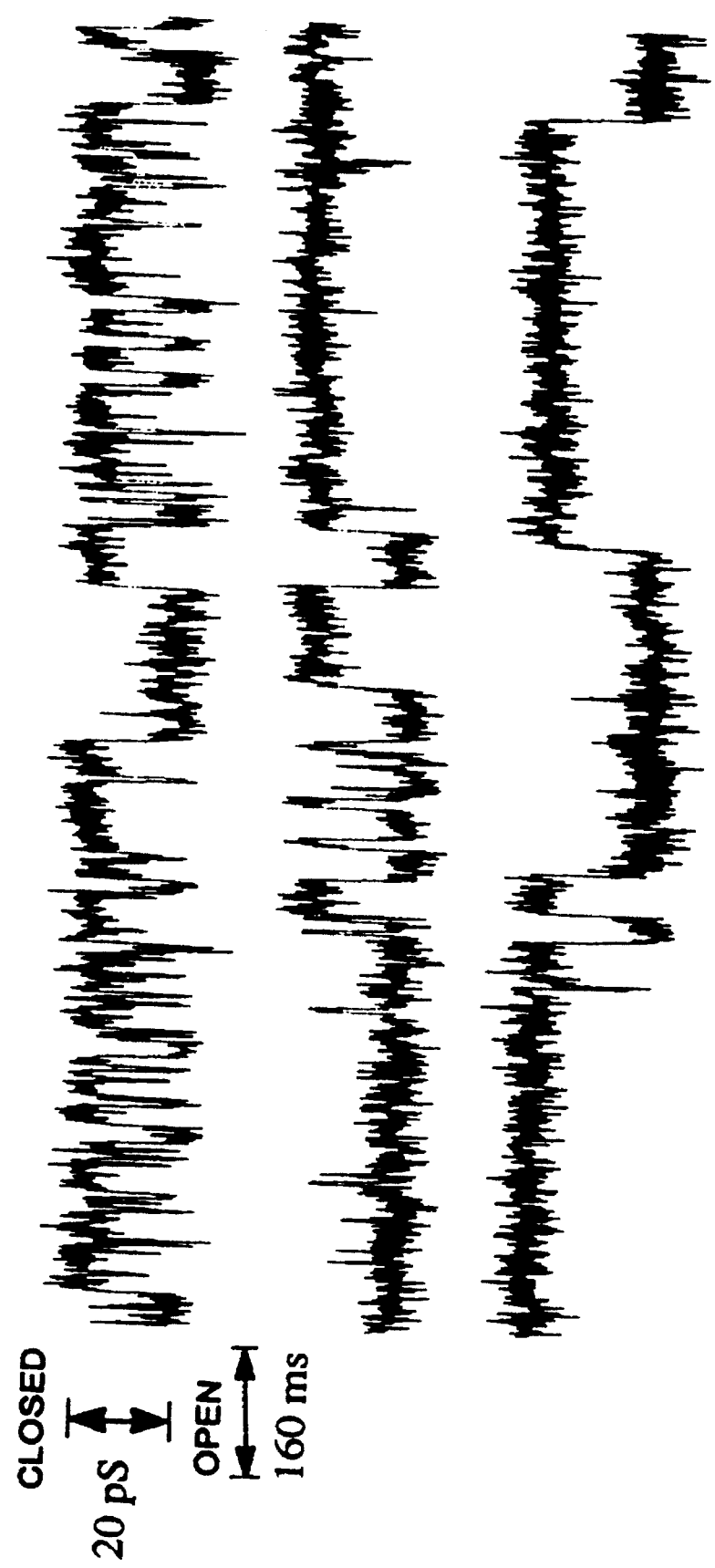
FIG. 10 is a series of waveforms from single channel recordings of lipid bilayer systems where the ion channels comprise tethered M2δ (A), monomeric M2δ (B) and M1δ (C)
Figure 10C:
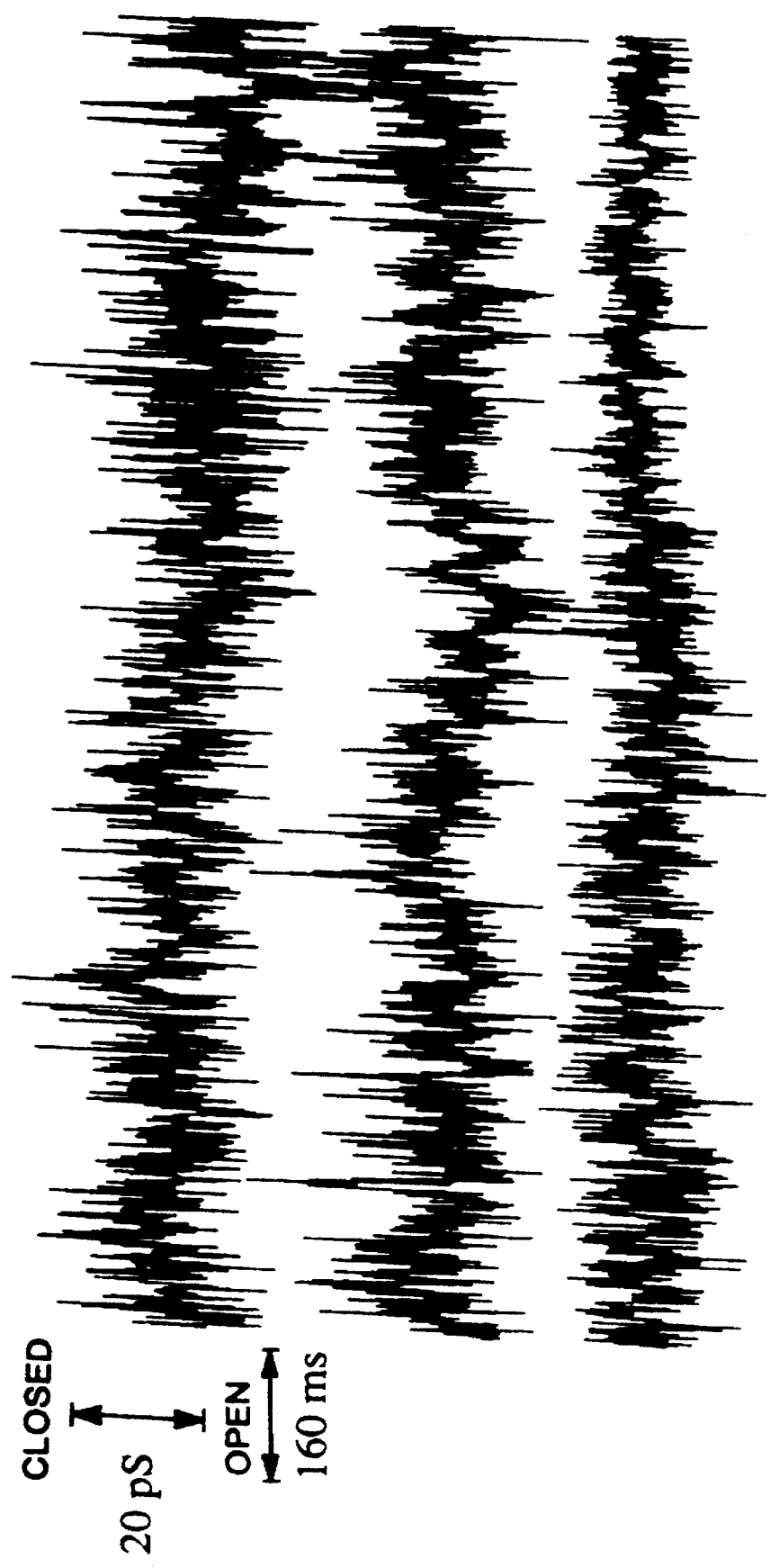

FIG. 10 represents single channel recordings from lipid bilayers containing tethered M2δ (FIG. 10A), in contrast to tethered M2δ with serine at position 8 replaced by alanine in each of the oligopeptides (FIG. 10B), and also in contrast to tetrameric M18 proteins (FIG. 10C). FIG. 10A shows the characteristics tethered M2δ ionic activity at higher resolution, and by comparison the analog synthetic porin with Ala substituted in the lumen of the pore (FIG. 10B) exhibits a lower V, consistent with published data recorded for mutant AChRs having the replacement at the same position. The consistency of these results between recombinant DNA technology and synthetic protein chemistry validates the present suggestion that the M2 segments form the AChR channel lining and further that serines exposed to the pore lumen contribute to the structure of the cationic binding sites.

The related but different M1S sequence does not form channels, however, as shown by the lack of unitary conductance steps in FIG. 10C. There is instead-a pattern of irregular transient fluctuations and baseline drift in the recordings, without a repeatable characteristic. Tests on the 9 amino acid backbone used as template without attached oligopeptides showed similar activity. These observations tend to verify the need for sequence specific oligopeptides for the assembly of ion conducting pore proteins.

Figure 11C:
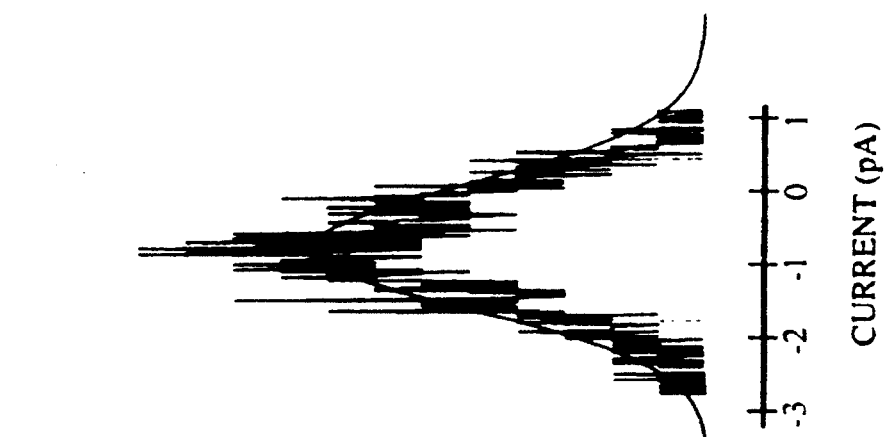
FIG. 11 is a series of current histograms, designated (A), (B) and (C) for the respective waveforms of FIG. 10.
Figure 11B:
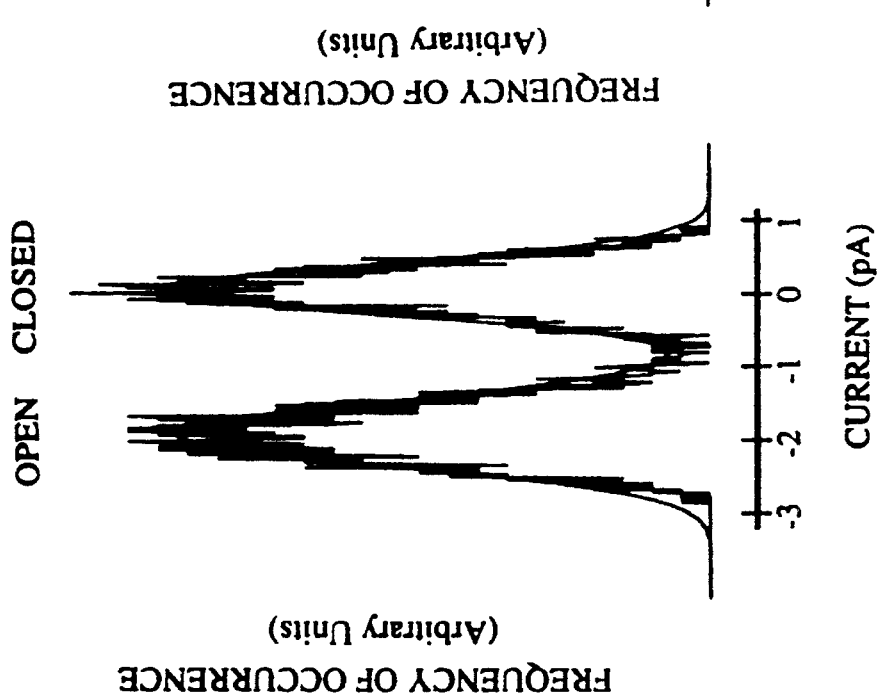
Figure 11A:
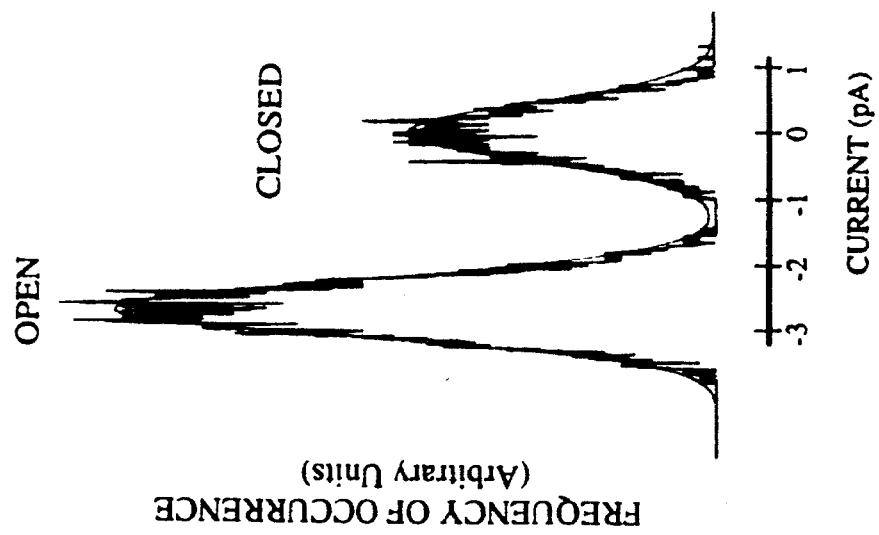

The contrast in characteristics is also clearly shown by the single-channel current histograms of FIG. 11, comprising 11A, 11B and 11C corresponding to the synthetic proteins of FIG. 10 above. Fitted Gaussian distributions (smooth curves) correspond to the channel closed state (peak at zero current) and the open state (peaks at 2.6 pA (FIG. 11A) and 2.0 PA (FIG. 11B). The calculated V values are 26 pS and 20 pS respectively. No peaks are discernible in FIG. 11C.

Purification of the Synthetic Porins

The proteins were purified by being subjected to multiple reversed phase HPLC runs. Proteins were dissolved away from the cleaved resin in $CF_3CH_2OH$ (TFE;99+% pure; Aldrich) and injected onto a vydae $C_4$ (semi-prep) #214 TP 1010 RP-column equilibrated in 75% buffer A (deionized/distilled water containing 0.1% HPLC-grade trifluoroacetic acid) and 25% buffer B (80% vol/vol) acetonitrile in water containing 0.1% trifluroacetic acid). Proteins were purified through a series of gradient steps followed by 30 min isocratic periods at 55%, 62% and 75% of solvent B. Samples were reinjected into a narrow-bore vydae $C_4$ RP column #214 TP54 equilibrated as described. Purified channel proteins were eluted by running the column isocratically at 70% of solvent B. Homogeneity was assessed by a third HPLC analysis on the same column and by capillary gone electrophoresis conducted in 20 m M citrate buffer (pH 2.5) at 38° C. on an ABI model 270A instrument.

Figure 12:
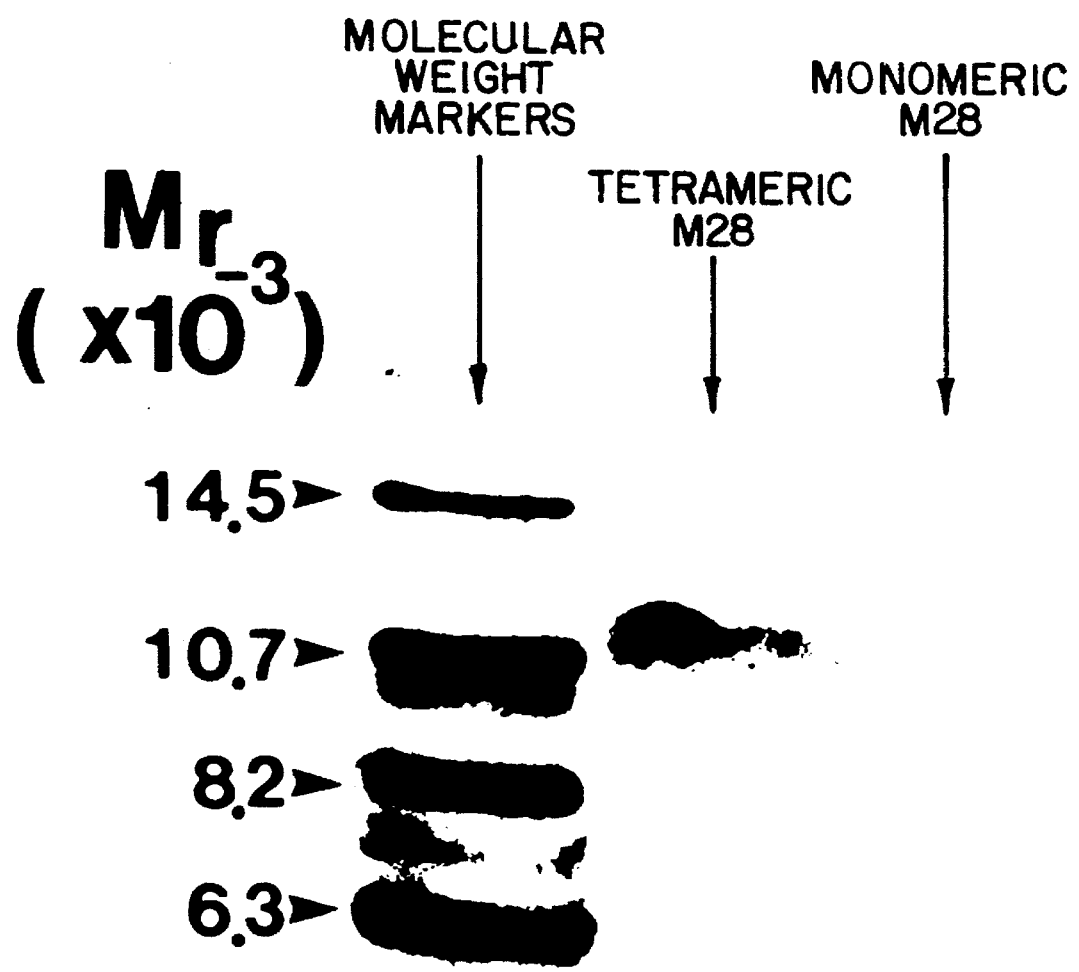
FIG. 12 is a printout of an SDS/PAGE analysis of tetrameric synthetic porins, wherein (A), (B) and (C) relate to different synthesized ion channels as designated.

Amino acid analyses of the purified peptides were undected to verify the amino acid sequences and confirm the predicted stoichiometry of the template and of the oligopeptides. SDS/PAGE analysis was conducted according to the laemmli method on 16% tricinegels. Molecular weight was estimated using CNBr-treated myoglobin molecular weight markers and protein concentration was determined. As seen in FIG. 12, the SDS/PAGE analysis shows that the tetrameric proteins migrate in SDS/polyacrylamide gels as single bands with Mr=11,000. This molecular weight is consistent with proteins containing 101 residues, such as the tetrameric M2δ. In contrast, the monomeric M2δ migrates with Mr>2000.

CD spectra show the occurrence of significant helical structures in the synthetic porins, including the M2δ, [Ala$^8$] M2δ and M1δ, respectively. CD spectra obtained from solutions of tetrameric synthetic porins in TFE, an organic solvent known to promote helix formation, exhibit the characteristic double minima at approximately 222 nm and 208 nm, with a prominent positive peak at approximately 195 nm. Calculated in helical contents for the tetrameric synporins are 44%, 45%, and 60% for M2δ, [Ala$^8$] M2δ, and M1δ, respectively.

Figure 13B:
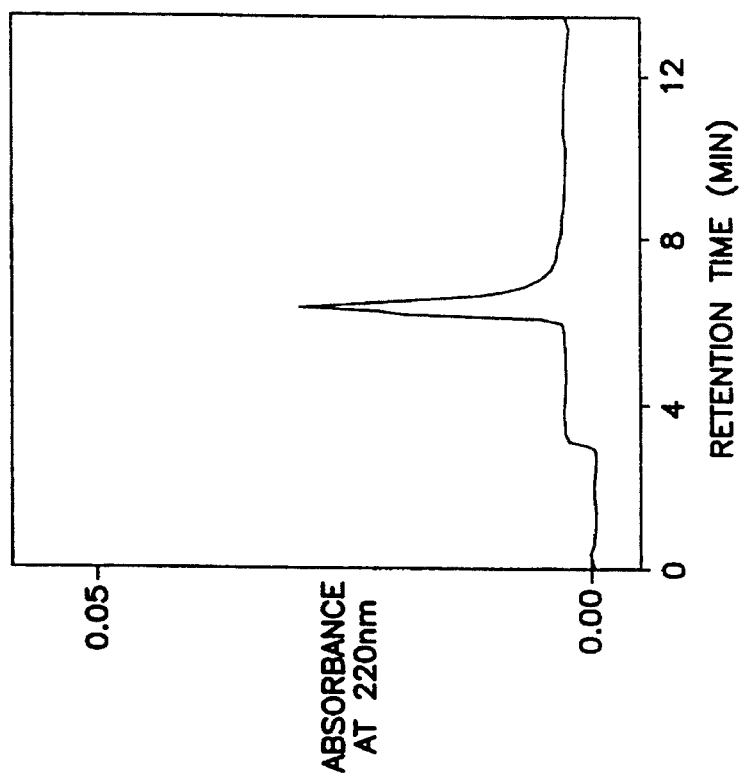
FIG. 13 comprises chromatograms showing absorbance vs. elution times (A) and absorbance vs. retention times (B)
Figure 13A:
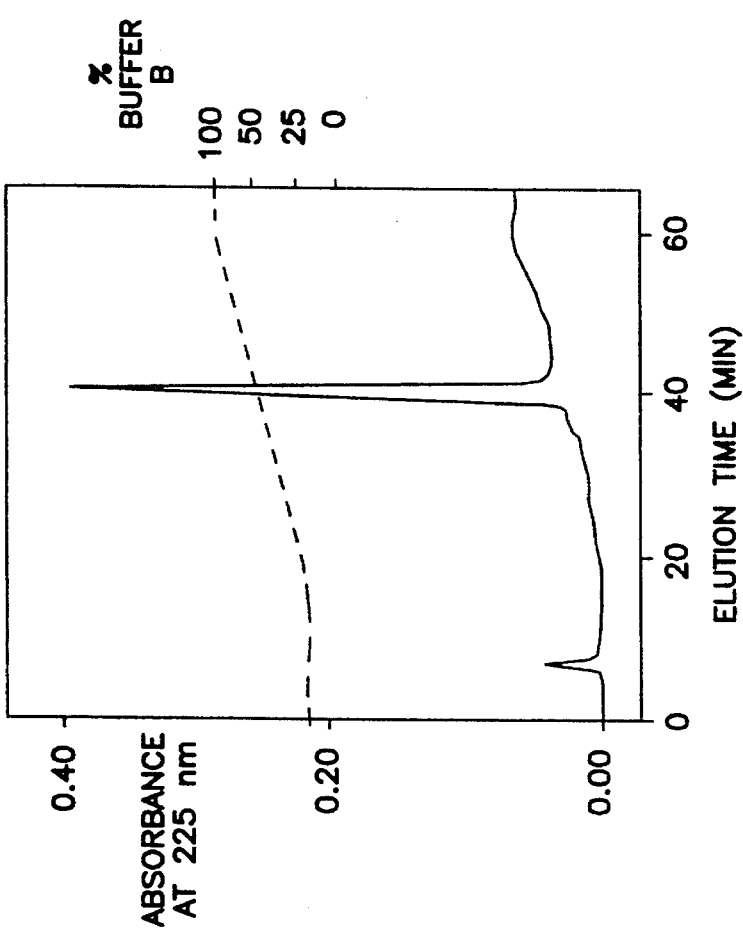

Further to demonstrate the purity of the proteins, their homogeneity was assessed reversed phase by HPLC analysis (FIG. 13A) and by capillary zone electrophoresis conducted in 20 mM citrate buffer (pH 2.5) at 38° C. on an ABI model 270A instrument. The proteins were eluted as well resolved peaks by both methodologies, as seen in FIGS. 13A and 13B.

Use of Synthetic Porins in Screening of Pharmaceuticals

The great variety of techniques now available for the generation of biochemical substances have led to the establishment of large libraries of pharmaceuticals whose properties and potential uses are unknown. While some predictive evaluations can be made based on theoretical studies and analogs to related known substances, there is perhaps a greater need for objective data. This need even extends to formulations which have been closely studied, because secondary and side effects cannot be dismissed in theoretical terms. The usual approach to acquiring objective data has been based on animal studies, which face increasing problems of availability, expense, convenience and social acceptability. Mimetic synthetic porins can be utilized in a variety of ways to provide useful data.

As one example, an individual pharmaceutical can be analyzed in detail relative to the response it engenders in a spectrum of ion channels. Because there are a number of different analog parameters involved in the ionic current readings obtained, a bank of data becomes available for defining potential uses of and problems with the material. As a different example, a number of pharmaceuticals can be tested relative to one specific ion channel, or a limited class of channels. Obviously also, synthetic porins can be used in other generalized and specific combinations. The availability of mimetic testing thus can be used in aiding drug design and verifying results of such design.

Uses of Synthetic Porins in Biosensors

Figure 15:
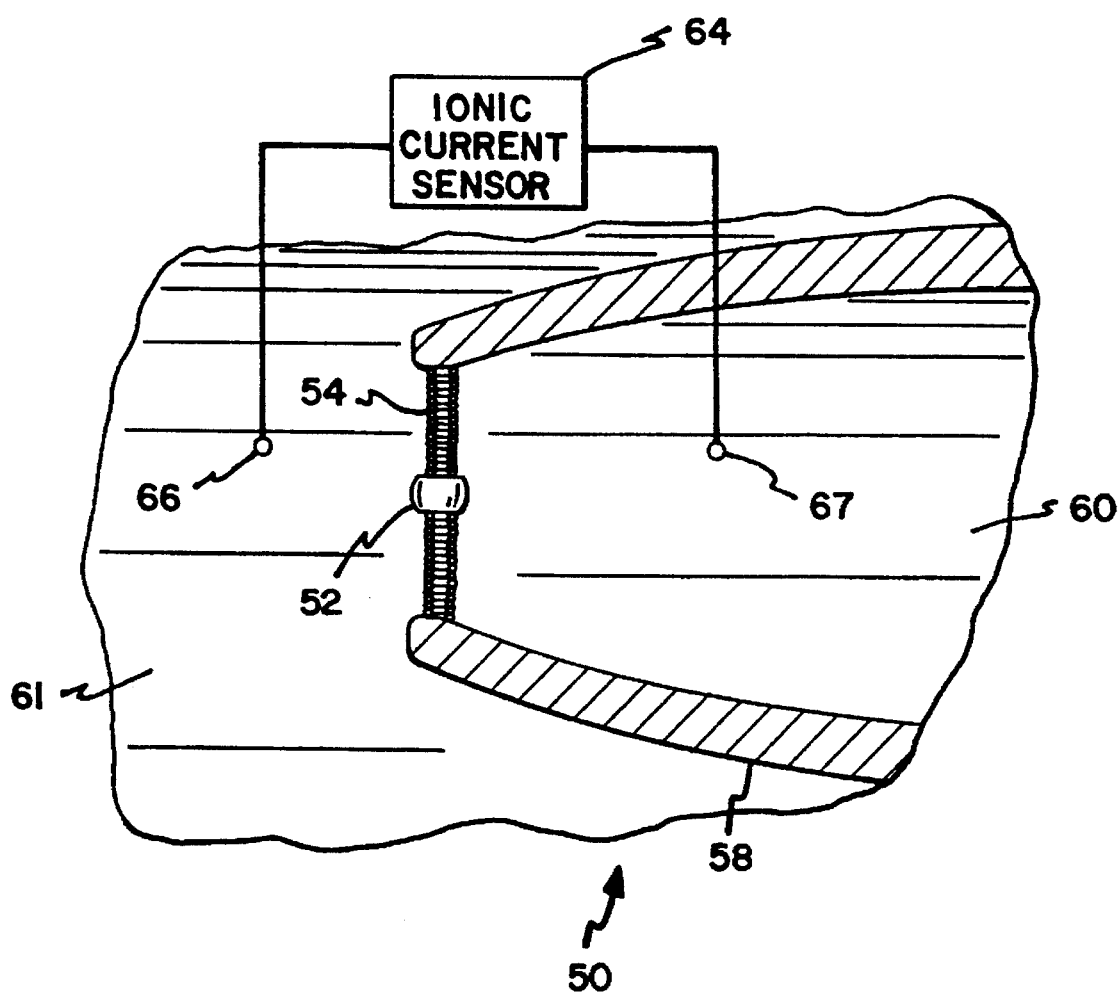
FIG. 15 is an idealized representation of a biological transducer device in accordance with the invention.

FIG. 15 depicts, in enlarged and simplified form, a biosensor 50 based generally on the single channel pipette device widely used in ion channel studies but incorporating a synthetic porin 52 embedded in a lipid bilayer 54 in accordance with the invention. Although an array of porins may be used, and the lipid bilayer 44 may be of natural or synthetic origin, the signal amplification properties of the biosensor 50 justify use in the single channel approach in many instances. In the unit, the tip of a micropipette 58 disposes the bilayer 54 and embedded synthetic porin 52 as a gating barrier between an aqueous ionic interior 60 and exterior 61 environment. An ionic current sensor 64 is coupled to electrodes 66, 67 in the exterior and interior 60, 61 to detect current flow.

With a suitably selected synthetic porin for a given compound, such as toxin, that is to be detected, the triggering event results in a measurable response at the ionic current sensor 64. Since the event occurs at the molecular level, the ultimate in sensitivity and miniaturization is achieved.

Self Assembly Methods

The self assembling homogeneous (then to light identical tethered peptides) or heterogenous (then to light peptides with at least one different tethered peptide) ion conducting channel peptides of this invention are prepared using methods that permit the introduction of only two or more different peptide chains onto a common polypeptide backbone. Such a capability permits the generation of a number of active channel proteins having multiple subunits, for example, αα, ααα, αβ$_1$, α1β$_1$, β1β$_2$, αβαβ, α1β1α2β2, etc.

The 2, 3 or multi-unit ion channels of this invention are prepared in two synthetic protocols. Protocol I involves a stepwise synthetic preparation of both template (or backbone) and active peptide while protocol II involves a template systhesis with sites for peptide synthesis and synthesis of the channel proteins or the preformed template.

In the first stepwise protocol I the synthesis occurs by a first synthesis, typically on a solid support, of a first peptide ending in an amino acid residue having at least two functional groups, a first group permitting the formation of a branch protein which can be an active channel peptide or another group permitting the continued synthesis of the protein tether or backbone. The branch protein typically is active in the protein channel while the backbone protein, at the end of the synthesis of all active subunits, ultimately forms a tethering peptide maintaining the peptide subunits in proximity promoting self assembly. Such a method can be used to form ion channels having two, three, four, five . . . n subunits, n being a number as large as 10, to meet the needs of the application. Preferably the protein has 3 to 7 peptides.

Alternatively, in the preformed template protocol (II) peptides can be formed on a template having two or more active sites for protein synthesis. A template or backbone polypeptide can be prepared having at least two synthetic sites with different functional groups on the polypeptide chain. One functional group can be used in the synthesis of one active peptide oligomer. Such synthesis does not affect the reactivity of the second functional group. After the first peptide oligomer has been synthesized, the second unmodified functional group can then be used as an origin or a synthetic site for the attachment and synthesis of the second polypeptide chain. These protocols are set forth conceptually in the following diagrams.

Protocol I Step-wise Synthesis

1. BEAD (Peptide A)—*
          |
          ‡

\* = a functional group useful as an origin of active peptide synthesis

‡ = a different, but stable origin of peptide synthesis that can remain in the peptide during synthesis 2. BEAD Peptide A—Peptide—*
         |           |
         OL‡         ‡

Peptide
3. BEAD—A——B——C—*
        |    |    |
        OL$_1$  OL$_2$   ‡

Peptide
4. BEAD—A——B——C——D—*
        |    |    |    |
        OL$_1$  OL$_2$  OL$_3$  ‡

A, B, C = peptide sequences

OL$_1$, OL$_2$, or OL$_3$ = active peptide subunits, or oligomers

BEAD = solid support material

Protocol Template First Synthesis

BEAD = support

X = any amino acid

\* = a functional group useful as peptide synthesis origin

‡ = a different, but stable origin of peptide synthesis that can remain in the peptide during synthesis OL$_1$ and OL$_2$ = active peptide oligomer

```
       *       ‡       *
       |       |       |
BEAD—X—(X)$_n$—X—(X)$_n$—X—(X)$_n$
``` n = integers 1,2,3, . . . ,n

```
       OL$_1$      *       OL$_1$
       |       |       |
BEAD—X—(X)$_n$—X—(X)$_n$—X—(X)$_n$

OL$_1$     OL$_2$     OL$_1$
       |       |       |
BEAD—X—(X)$_n$—X—(X)$_n$—X—(X)$_n$
```

An inspection of both synthetic protocols indicates that each can be used for the stepwise synthetic preparation of branched peptides linked to a template or backbone wherein the subunits can be homogeneous or heterogeneous.

Both protocols above begin with initial attachment of an amino acid residue or residues on a solid support. Generally, the initial amino acid residue(s) can be attached to a resin through the amino acid carboxyl group to an active group, such as a t-boc or f-moc amino acid substituted resin, on the resin. The synthesis in both protocols initially continues with attachment of additional amino acids to the N-terminal amino group of the growing peptide attached to the solid support material.

The backbone or template proteins contain sufficient amino acids to provide the correct spatial confirmation of the protein subunits after synthesis is complete. Typically, the templates are generally less than about 25 amino acids in length, but they are more commonly less than 15 and are most commonly less than 10 amino acids in length.

The peptide or oligomers that are synthesized on the functional groups in either protocol can be synthesized beginning at a carboxyl terminus forming parallel relationships with adjacent protein subunits. The protein subunits can be of any arbitrary length, however the synthetic channel proteins are typically less than 50 amino acid residues and commonly are less than 30 amino acid residues. Before synthesis of the active protein subunits begins, other compounds can be reacted at the active functional group. Spacer compounds can be reacted at the functional group to provide the ability to adjust the spatial separation of the active subunit from the protein backbone or template. Such spatial separation from the backbone permits adjustment of the position of the protein subunit with respect to the next adjacent protein subunit to ensure that the correct portions of each adjacent subunit interact with the appropriate location of an adjacent subunit.

Once formed, the protein subunits can self assemble, preferably into amphipathic α-helices, although β sheets or other natural conformations are also possible. The protein subunits can also be treated to introduce non-natural secondary or tertiary structures.

Virtually any ion channel protein can be used in the synthetic ion channel, which can contain two or more channel subunits. Protein subunits forming active ion channels can be found from the analysis of primary structures of naturally occurring peptides and glycol proteins. In proposing possible structural models of active channel proteins that may account for aspects of ion flow through the channel as well as voltage dependent channel opening and closing (gating), and which are consistent with the primary structure, we assume that a number of conditions exist. Membrane spanning regions have an organized secondary structure, probably α helical in the absence of hydrophobic leader sequences suggesting both C- and N-terminals. An even number of transmembrane segments per homology region exist for the voltage dependent changes in dipole moment that are observed as gating current. This implies displacement of charges buried within the intramembranous, hydrophobic interior of the protein. At physiological pH, glutamate and aspartate residues are negatively charged and lysine, arginine, and asparagine groups are positively charged. The location of these charged groups within the protein membrane interior would be energetically favored by the formation of ion pairs. Ion diffusion through the channel proceeds by a water filled pore whose walls consist of amphipathic structures including one or more hydrophilic groups within the pore. A one-dimensional representation of the cytoplasmic, transmembrane, and extra cellular domains establishes four homology regions each consisting of eight transmembrane spanning helical segments. Adjacent segments traverse the membrane; in anti-parallel orientation.

This tertiary structure model of the channel shows the four homologous regions organized in a radially-symmetric array.

Identification of Ion Channel Protein Sequences

The primary amino acid sequence of the suspected ion channel proteins can be obtained by isolating the proteins from the natural membranes; from DNA sequences of gene segments coding for the proteins; from RNA sequences or from RNA sequences coding for the proteins. The protein primary structure can then be analyzed by computer methods to find homologous regions in the primary sequence that can theoretically align to create the parallel or anti-parallel sequences. Synthetic proteins can then be synthesized containing the homologous regions or portions thereof. The minimum requirements of the protein sequence, used in the ion channel, is that the sequence have sufficient length to span the lipid bilayer and form α helical amphipathic structures which can cooperate to form the preferred ion channel structures in conjunction with the template or backbone sequence discussed above. Further information regarding the computer aided procedures used to identify channel forming segments in the sequence of the receptor proteins can be found in R. E. Greenblatt et al, 1985 FEBS. Lett. 1973, No. 2, pp. 125–134; M. Noda et al, 1984 Naturel 312, 121–127; T. E. Creighton, 1984 Proteins, W. H. Freeman, New York; J. Finer-Moore and R. M. Stroud, 1984, *Proc. Natl. Acad. Sci. U.S.A.* 81, 155–159. The primary protein sequence was obtained in digital form from the NEWAT data base. Hydrophobicity plots were determined as described in J. Kyle and R. Doolittle (1982) *J. Mol. Biol.* 157, 105–132. The power spectrum of the hydrophobic density was obtained using published methods, J. Finer-Moore and R. M. Stroud, 1984, *Proc. Natl. Acad. Sci. U.S.A.* 1981, 155–159 employing a window of 25 residues and normalizing with respect to the mean spectral density. The structure prediction algorithm of J. Garnier, D. J. Osguthorpe and B. Robson 1978 *J. Mol. Biol.* 120, 97–120. Homologous sequences were aligned using the "structure-genetic" matrix with a length-independent dependent penalty of 5.0, as described by D. F. Feng et al, 1985, *J. Mol. Evol.* 21 112–125 as the basis for a metric. Helical nets were drawn after C. Chothia 1984, *Annu. Rev. Biochem.* 53, 537–571. Molecular modeling was conducted using the "MMS" program developed at the University of California San Diego, Chemistry Department Computer facility.

One synthetic sodium or potassium channel peptide has been found that contains 22 amino acid residues. The synthetic peptide mimics the electrical properties of a voltage dependent sodium channel. The single channel conductance of the most frequent event is 20 pS in 0.5M sodium chloride, the single channel open and close lifetimes are in the millisecond time range, the synthetic channel discriminates cations over anions, but is nonselective between sodium ion and potassium ion. The synthetic channel displays no specific voltage dependence. These energetic considerations suggest that the preferred structure of the synthetic channel is a four parallel amphipathic α helix structure. The preferred sodium channel sequence is as follows: XPWNWLDFXVITMXYXTXXXXX, wherein each (X) represents any possible amino acid residue. The most preferred sodium channel sequence is as follows: XPDWNWLDFTVITFAYVTEFVDL.

Similarly, we have found a synthetic peptide that mimics an acetylcholine receptor (AcChoR) M2δ subunit which we have discovered to form discrete ion channels in lipid bilayers. Other transmembrane segments of related peptides found in the acetylcholine receptor have no ion channel properties. We have found that this ion channel peptide appears to form an ion channel from two to five amphiphatic α helix units in the channel. The preferred amino acid sequence is as follows: EKMSXAISVLLAQXVFLLLX-SQR where each (X) is any possible amino acid. The most preferred sequence is as follows: EKMSTAISVLLAQAV-FLLLTSQR.

Incorporation of Synthesized Ion Channel Proteins in Lipid Bilayers

Planar lipid bilayers into which the synthetic ion protein channels can be incorporated are prepared using commonly available and well understood lipids and bilayer formation techniques. For example, planar bilayers can be formed by hydrophobic apposition of two lipid monolayers initially formed at an air-water interface. The electrical properties of such protein-free bilayers can be examined using known techniques. Peptides can be incorporated into the bilayers from mixed lipid-peptide monolayers. Purified peptide (10–100 micromoles in a chloroform/methanol 1:1) can be mixed with lipid and achieve a final peptide lipid molar ratio in the range of about 1:100–1:10,000.

Suitable lipids for the formulation of the bilayer membrane for use in the present invention include phospholipids such as phosphatidic acid, diphosphatidyl glycerol, phosphatidyl glycerol, phosphatidyl choline, phosphatidyl ethanolamine, phosphatidyl serine, phosphatidyl inositol, phosphatidyl compounds with acyl chains such as mono of dipalmitoyl, mono or dimyristoyl, mono or diphytanoyl, mono or distearoyl, mono or dioleoyl; sphingolipids such as ceramides and cerebrosides; glycol lipids such as mono or digalactosyl diglyceride; and other lipids or lipid analogs such as glycerol, monoleate, and eggphosphatidyl choline. The preferred lipid is 1,2-diphytanoyl-sn-glycero-3-phosphocholine. We have found that the ion channel containing membranes formed with our techniques are stable for extended periods of time at laboratory temperatures.

Biosensor Manufacture

The above described channel proteins mediate the transfer of information across synthetic cell membranes because the channel proteins are exquisitely sensitive and extremely efficient materials. The invention embodies a blend of lipid bilayer technology and peptide synthesized technology to form a new biomolecular species that can function in a bioactive element in a biosensor device. The bilayer alone or the peptide alone cannot act as a sensor until assembled with the active protein inserted into and spanning the membrane. The channel proteins can sense the presence of a chemical ligand, neurotransmitter or other chemical substance. The channel proteins can also detect an electrical impulse or transmembrane voltage (or applied potential difference). Once a chemical ligand, or electrical impulse, has been sensed by the membrane protein channel, the detection event can be amplified by the passage of up to $10^8$ ions or more per second across the insulating bilayer lipid membrane through the ion channel protein pore.

Such a selective ion transport property can be used in a biosensor. The biosensors of the invention can be formed in a compact and portable format. The biosensors comprising an ion channel protein in a bilayer lipid membrane can detect the presence of environmental stimulus in the form of the presence of a chemical ligand or electrical potential to produce changes in the channel protein. The biosensors of the invention typically take the form of an aperture or space into which the bilayer lipid membrane containing the channel proteins of the invention can be placed. The lipid membrane of the invention wholly covers the aperture or space of the biosensor sealing the interior of the biosensor from the exterior source of stimulus. One or more lipid bilayers can be mounted in one or more apertures of the structure. The current and voltage changes across the membrane can be recorded using appropriate electrical measuring devices. The imposition of an electrical potential or the binding of ligands to the channel proteins triggers leakage of ions down concentration gradients.

The biosensor device of the invention can consist of a lipid bilayer containing active membrane ion channel proteins which separates two aqueous electrolyte filled compartments, each compartment containing a nonpolarizable electrode which is used to sense the conductivity of the membrane. The lipid bilayer and the ion channel proteins must be compatible in the completed device. A shield can be placed across the fragile lipid bilayer to protect the bilayer from disturbance from external influences. The shield may consist of simple porous screens semi-permeable membranes, in situ polymerized film, layers, etc.

Layering on Electrodes

The use of ion channels in biosensor configurations may as discussed in U.S. Pat. Nos. 4,637,861, 4,661,235, 4,776, 944, 4,824,529, 4,849,343 and Statutory Invention Registration H201, entail the use of special membrane supports and electrode layers as disclosed in those documents. The greater durability and stability afforded by synthesized structures in accordance with the invention, and the flexibility in design derived from template assisted synthesis, afforded much greater potential for biosensor systems and devices. The problems involved in layering the ion channels and membranes are both biochemical and electrical in nature. Materials which form a close and nontoxic interface with biological material are generally low efficiency conductors, while good conductors (such as metals) tend to be toxic or reactive when in close association with the protein assemblies. Synthesized channels which are template tethered help to achieve an improved balance of characteristics because of their lower sensitivity and the opportunity they afford for adjustment of parameters.

Size Varying Gates

Figure 14:
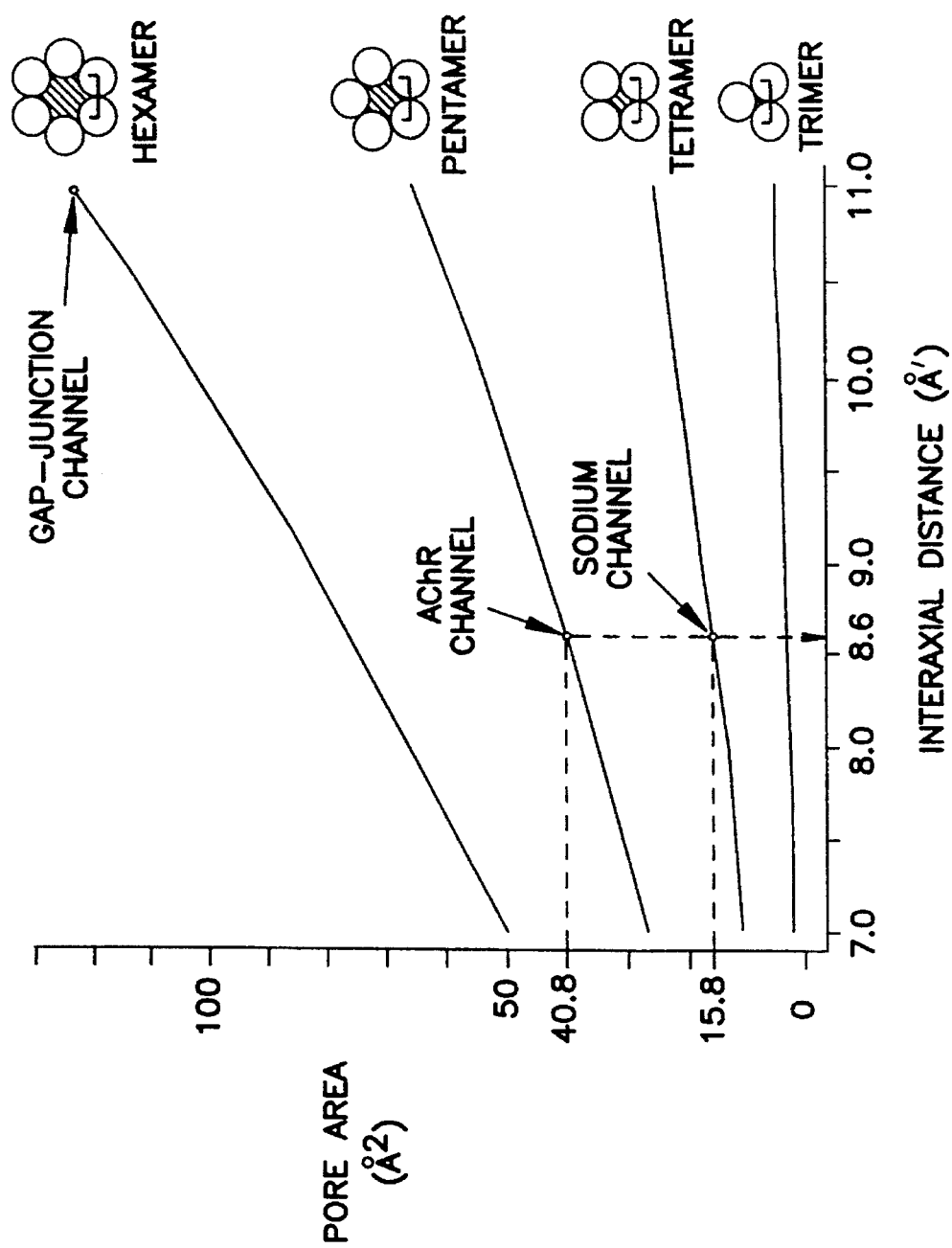
FIG. 14 is a chart of pore area vs. interaxial distance for different channel structures.

The synthesized ion channel affords the capability for forming size selective gates, so that ionic permeability can be made responsive to the size of constituents in the ionic medium as well as other factors. As shown in FIG. 14 for various native channels, there are substantial differences in pore area between the tetrameric, pentameric and hexameric channels, given the interaxial difference that exists between submits. The pentameric AChR channel and Tetrameric Sodium channels have pore areas of 40.8 A and 15.8 A respectively, given the same interaxial distance of about 8.6 A. The gap channel junction is a hexamer having an interaxial distance of about 11.0 A, and a pore area of about 130 A.

FIG. 14 also indicates the much smaller pore area defined by a trimeric structure. Since synthesized peptides forming ion channel proteins in accordance with the invention can be reliably attached and positioned relative to the tethering points on a template, and since three to seven peptides are feasible, a different parameter of design variability is provided. The gating function, in terms of conformational change in response to a sensed condition, may be varied somewhat, and thus become more, or less, mimetic of the native channel. However, ionic flow can also be modified in response to preselected conditions in other ways. For example, by using a large pore size channel, the channel lining can be modified, as by tethering a binding site, such as an epitope, for a specific constituent in the pore area. This would block the channel by binding to the selected constituent, whether the constituent comprises an antibody, protein or other physiologically active substance. Thus size varying gating in this manner permits both further tailoring of responses and the addition of new functions.

The lipid bilayer containing biosensors of the invention can find application as detectors of environmental stimuli such as vapors or dissolved compounds such as toxins, insecticides, food additives, drugs, etc. The biosensor of the invention can be used as a screening device for drugs acting as blockers or modifiers of ion channels in brain, skeletal, heart muscle, or other natural source. The synthetic protein channel containing biodetectors can be used as molecular models for the design and development of drugs targeted to receptors in brain and muscle and other nervous system ion channels.

Specific Example of a Synthetic Protocol for a Preferred Template

We have synthesized a tethered parallel tetramer with four M2δ 23-mer peptides with amino acid sequence (EKM-STAISVLLAQVAFLLLTSQR) attached to a multi-functional carrier template having an at least seven amino acid backbone wherein in the backbone four basic amino acids of the general structure with an R bonded to the C/C, wherein R has a terminal nitrogen group substituted with a removable protecting group that can be used as a linkage to the proteins attached to the peptide after template peptide synthesis.

The preferred protecting groups are f-moc* or t-boc*. The template can take the form of: $B'(X)_n$ $B'(X)_n$ $B'(X)_n$ $B'(X)_n$. Where any B' is a basic amino acid containing a terminal nitrogen substituted with a protecting group. X is any arbitrary amino acid and n is an integer of about 1 to 50. (* f-moc=9-fluorenyl methoxy carboxyl and t-boc=t-butoxy carboxyl).

The original template synthesis took the form: $K^1$ K $K^2$PG $K^1$ E$K^2$G wherein $K^1$ is derived from f-moc substituted E amino lysine. The other amino acids in the template were derived from N-substituted t-boc amino acids. Once the peptide template assembly is complete, the protecting groups on the N-substituted lysine side chains were deprotected. The protection groups can either be removed simultaneously for substitution with the fully assembled protein or a step-wise synthesis of the protein. For the staggered synthesis a template is assembled using two different orthogonal protecting groups each deprotected selectively by alternate chemistries. A representative protocol has the following template: $A_cK^1$ K $K^2$PG $K^1$ E$K^2$G, synthesized using t-boc chemistries where (1)=$N^\alpha$–t-boc, $N^\epsilon$–NPYS lysine and (2)=$N^\alpha$ t-boc $N^\epsilon$–f-moc lysine. The NPYS and f-moc groups can be deprotected individually by triphenyl phosphine and organic base, respectively. This approach allows for the attachment of two separate helical segments to the backbone.

Alternative Example of a Synthetic Protocol for a Template

In an alternative protocol, the template or protein backbone providing attachment point for the protein subunits is not preformed, but is formed part-wise in a staggered synthesis of template portions each portion being prepared prior to the formation of each subunit portion as described above.

This approach can be accomplished quite simply using $N^\alpha$-t-boc, $N^\epsilon$-t-boc lysine and analogs of that substituted lysine residue using other N-substituted basic amino acids, at a branch point. The lysine derivative has the following structure:

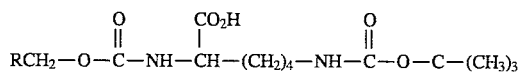

Wherein R is:

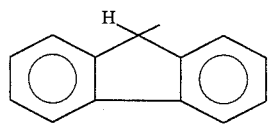

The lysine reagent having both an N alpha-f-moc and an epsilon t-boc functional group produces a difunctional branching point that can be utilized to both begin the synthesis of a protein subunit and extend the synthesis of the backbone or template protein after the subunit synthesis is complete. Such a synthesis occurs as follows. A solid support for the synthesis of peptides is one or more amino acids selected arbitrarily from the typically simple amino acids such as alanine, valine, glycine, serine, etc. that can be attached to the solid support using known methodology. The protein synthesis typically is initiated by the attachment of the carboxyl functionality of the amino acid to the solid support. When the initial peptide sequence is formed, the end terminal amino acid is reacted with the f-boc, t-boc substituted lysine material. The carboxyl of the substituted lysine residue bonds to the N-terminus of the peptide chain on the solid support leaving the f-boc and t-boc residues available for deprotection and subsequent synthetic reaction. Preferably, the t-boc functional group of the lysine residue is removed with strong acid catalyst, typically trifloacetic acid or concentrated formic acid, generating a free amino group. T-boc chemistry is used with conventional reactive protocols to introduce a peptide or amino acid oligomer on the epsilon-$NH_2$ lysine group. Such oligomers are typically comprised from about 5 to about 100 amino acid residues. The residues are selected such that they will form active ion channel structures upon the completion of the protein synthesis. Such structures often naturally form α-helices or β sheet proteins. Once the protein subunit is complete, the subunit is acetylated using acetic anhydride or other such reagents. The remaining f-boc functional group on the branch point lysine amino group is removed with basic catalysis typically piperidine exposing the α-amino group for further reactivity. The t-boc chemistry is used in conventional protocols to introduce one or more amino acid residues into the α amino group of the lysine residue in the polypeptide chain. When a sufficient number of amino acids have been attached to lysine alpha amino acid, the growing chain is then reacted with the f-boc t-boc lysine providing the bifunctional branch point. The protocol set for the above is then completed for the next protein subunit and to extend the protein backbone or template molecule until the protein contains 2, 3, 4, 5, 6 or more branch segments depending on the number desired for the active protein channel and the desired backbone sequence.

These synthetic protocols set forth above produce peptides having an orientation of the amino acid residues directed from the carboxyl to the amino direction. This limits the synthetic protocol to generating helices that have parallel orientations or parallel helical dipoles. To create an anti-parallel structure, one can synthesize in the reverse amino acid sequence which provides the correct sequence but typically does not provide the correct dipole moment. In order to prepare the correct protein dipole orientation, D-amino acids could be coupled or a different site-specific bifunctional coupling agent introduced into the protein template backbone in either the first or second protocol. Such a bifunctional coupling agent has at one terminus of the molecule an activated carboxyl group that can react with an amine functionality of the protein or peptide and at the other end of the coupling agent has a reactive functional group that can be used to attach the protein peptide coupling agent residue onto the template backbone. In a preferred format, the complete synthesis of the anti-parallel helix is completed and then coupled by the bifunctional coupling agent to a reactive site on the template to form an anti-parallel array adjacent to a parallel array to provide the active parallel/anti-parallel end channel. Such a bifunctional coupling agent comprises succinimidyl-4-(N-maleimido-methyl)-cyclohexane-1-carboxylate. The succinimidyl substituent on the carboxylate functionality of a molecule can react with alpha amino groups of proteins or peptides. The unsaturated group of the maleimido functionality of the molecule can react with sulfhydryl groups in the protein template or backbone to attach the protein or peptide sequence into the backbone. Under certain circumstances, the parallel/anti-parallel helices may not align properly owing to differing lengths in the spacers used in the manufacture of the active proteins. In such an instance, additional amino acids can be added at the branch points to lengthen the parallel units for proper alignment with the anti-parallel units. Additionally, the primary sequences of the parallel and anti-parallel helices can be experimented with to determine sequences that can be aligned even with differing lengths of spacers.

Chemical Synthesis of AChR T-M2δ Ion Channel

The synthesis of the 101 residue four helix bundle tethered to a template was accomplished by employing a two step procedure. A template of nine residues was synthesized initially such that four branch points were generated that were all cis relative to the plane of the nine amino acid peptide. The N-terminal residue was then blocked and the branch points deprotected. In the second step, four identical helices corresponding to the putative transmembrane M2δ segment of the Torpedo californica acetyl choline receptor (AChR) subunit were attached in a step-wise manner. The completed AChR-template and M2δ was cleaved from the solid phase support, solubilized and purified by reverse-phase chromatography.

The template was synthesized using automated solid-phase synthetic techniques starting with 0.2 m moles (300 mg) of a t-butyloxycarbonyl-glycine-PAM resin. The resin was deprotected with neat trifluoroacetic acid (TFA) for 5' followed by flow through washes of dimethylformamide/n-methyl-pyrolidone (DMF/NMP) 70:30.

The resin was then neutralized with 50% diisopropylethylamine in DMF/NMP (70:30). The next amino acid (1.0 m mole) was added as the preformed symmetric anhydride.

The species was generated by the reaction of a protected amino acid with dichlohexylcarbodiimide in a 2:1 ratio in dichoromethane (DCM). The DCM in the activated amino acid mixture was then replaced with DCM/NMP 70:30. The coupling of the activated amino acid to the growing peptide chain was allowed to proceed for 20 minutes. The coupling step was repeated with a second aliquot of activated amino acid to ensure high coupling efficiency >99% per residue. The fully coupled resin was then subjected to deprotection in the presence of TFA to generate the next site for elongation of the peptide. The next amino acid was then added (again as the preformed symmetric anhydride). The cycles were then repeated until all of the desired residues had been incorporated. In this manner the template:

NH$_2$—K* K$^±$ K* P G K* E$^+$ K* G—PAM resin was generated;

where E$^+$=1-glutamic acid—γ benzyl ester

K$^±$=N-ε-2-chlorobenzyloxycarbonyl-1-lysine

K*=N-ε-(9-Fluorenyl methoxycarbonyl)-1-lysine.

The N-terminal lysine was then acetylated with acetic anhydride 20% in DMF/NMP (70:30) until the free amino group was longer detectable by reaction with ninhydrin. The fluorenylmethoxycarbonyl groups (f-moc) were then removed using 20% piperidine in DMF (20'). The resin was then washed with DCM and stored in vacuo. The yield for this portion of the synthesis was 750 mg of peptide bound to resin.

For the second phase of the synthesis 0.04 m moles (150 mg) of template-resin was used with 1.0 m moles of amino acid per coupling. Triple couplings were used to ensure high coupling efficiencies. Chemistries similar to those presented in the template synthesis section, with the exception that the amino acids were all coupled as the hydroxybenzytriazole esters, were employed to add the 23 residue peptide AChR M2δ:

E K M S T A I S V L L A Q A V F L L L T S Q R (4x).

The yield of the final peptide/resin was greater than 800 mg.

The peptide/resin was washed with dichloromethane and dried overnight. Cleavage and full deprotection of the molecule was carried out using 250 mg of peptide/resin in the presence of 0.33 ml of scavenger (p-cresol) and 0.33 ml of reducing agent (p-thiocresol). Anhydrous HF (8–10 ml) was prescrubbed with the free radical scavenger anisol (1.0 ml) in the condensing vessel at –40° C. The HF was then distilled over into the reaction vessel. The cleavage reaction was carried out at –10° C. for 30' followed by 0° C. for an additional 60'. The HF was removed at the end of the reaction and the cleavage mixture was washed with 100 ml of anhydrous diethylether. The resultant precipitate that contained the cleaved peptide and vinyl benzene resin was collected, dried and stored in vacuo over KOH.

The peptide was separated from the resin by dissolving 10 mg of the peptide precipitate in 0.5 mil trifluoroethanol (TFE) 0.1 ml distilled water. The solution was intermittently vortexed over a period of 5'. The solution was then centrifuged for 2' at 10,000 xg. The supernatant was then passed over a Sep-pak™ C18 reverse phase cartridge. Before applying the peptide the column was first washed with 50% acetonitrile in water and then equilibrated in distilled water. The entire 0.6 ml of solution was passed over the column. Two 1 ml washes with water were performed. The peptide was eluted with three washes of 50% acetonitrile in water. One mil fractions were collected during this procedure and each was assayed for the presence of protein. The only fractions that contain appreciable amounts protein were the first two milliliters of elution with the 50% acetonitrile in water. These fractions were further analyzed by HPLC analysis.

Purification of Proteins and Analytical Data Therefrom

High pressure liquid chromatography analysis of the T-AChR M2δ peptide was carried out using a reverse-phase system. We equilibrated a 12.5 cm C18-RP column (LKB Superpak™) with buffer A (deionized/distilled water containing 0.1% HPLC grade trifluoroacetic acid). The fraction containing the highest protein concentration (6.7 mg/ml) was analyzed and a 20 μg injection was performed. The components of the peptide solution were eluted using a 60' gradient to 100% solvent B (80% acetonitrile in water containing 0.1% TFA). The flow rate throughout the chromatography was maintained at 0.3 ml/min.

The eluents were monitored at a wavelength of 225 ηm. The peptide eluted at approximately 45% of buffer B (36% acetonitrile) as a single sharp peak and integrated to >80% of the material eluted from the column. This purified material was then reduced to remove the acetonitrile and made up to a final concentration containing 30% trifluoroethanol is water. This material was then analyzed for its ability to form ion Conducting channels in synthetic bilayers. The peptide was also analyzed by SDA-PAGE. The mobility of the peptide was shown to be 11 kDa which was consistent with a protein containing 101 amino acid residues.

Stepwise Procedure for Chemical Synthesis of AChR T-M2δ

The synthesis of the 101 residue for four helix bundle was accomplished by employing the step-wise procedure. Each of the four helices was synthesized step-wise in conjunction with the step-wise synthesis of the tether or template (backbone). The step-wise synthesis occurs in a fashion such that each protein was generated cis relative to the plane of the peptide backbone. The completed protein was cleaved from the solid support solubilized and purified by reverse osmosis chromatography.

The template was synthesized using automated solid phase synthetic techniques starting with 0.1 m moles (300 mg) of t-butyloxycarbonyl-glycine-PAM resin. The resin was deprotected with neat trifluoroacetic acid (TFA) for 5 minutes followed by flow through washes of dimethylformamide/n-methyl-pyrolidone (DMF/NMP) 70:30. The resin was then neutralized with 50% diisopropylethylamine and DMF/NMP (70:30). The next amino acid (0.10 m mole) was added as the preformed symmetric anhydride. The species was generated by the reaction of a protected amino acid with dicyclohexylcarbodiimide in a 2:1 ratio and dichloromethane (DCM). The DCM in the activated amino acid mixture was replaced with DCM/NMP 70:30. The coupling of the activated amino acid to the growing peptide chain was allowed to proceed for 90 minutes. The coupling step was repeated with a second aliquot of activated amino acid to ensure high coupling efficiency greater than 99% per residue. The fully coupled resin was subjected to deprotection in the presence of TFA to generate the next site for elongation of the peptide. The next amino acid which was added was an alpha n-f-moc-n-epsilon t-boc lysine was then added (again as the preformed symmetric anhydride). The first helix was coupled with the lysine residue at the amine group deprotected of the t-boc residue. Upon completion of the synthesis, the N-terminal glutamic acid was deprotected with TFA and subsequently, acetylated with acetic anhydride. For the second phase of the synthesis, the branch point lysine was deprotected at the N-α position using the organic base piperidine (20% in DMF for 20 minutes). A series of t-boc chemistries were employed to add the next two residues (namely, a glutamic acid gamma benzyl ester and an N-α f-moc-N_ε-t-boc lysine). The side lysyl t-boc was deprotected with TFA and a second M2δ sequence was added using t-boc chemistry. The steps were repeated as outlined above to form a peptide was four M2δ units attached to a backbone.

Chemical Synthesis of Calcium Channel

Using a synthetic preparation sequence substantially the same as was used in preparing the above template and AchR t-M2δ ion channel shown above, an active calcium channel was prepared with an active pore defined by forming peptides of the single letter code sequence:

D-P-W-N-V-F-D-F-L-I-V-I-G-S-I-I-D-V-I-L-S-G-template.

Chemical Synthesis of a GABA Receptor

Using a synthetic preparation sequence substantially the same as was used in preparing the above template and AchR-T-M2δ ion channel and $Ca^{++}$ channel shown above, an active GABA (gama amino butyric acid) receptor was prepared with an active ion channel pore defined by the single letter code sequence:

A-R-T-V-F-G-V-T-T-V-L-T-M-T-T-L-S-I-S-A-R-TEMPLATE.

The above discussion of the invention and the preferred embodiments of the invention provides sufficient information for the skilled artisan to understand the invention. However, since many embodiment of the invention can be made without departing from the spirit and scope of the invention, the invention resides in the claims hereinafter appended.

We claim:

1. A sequential method of preparing a polypeptide backbone and active ion channel subunits comprising:

(a) preparing a polypeptide backbone portion having 1 to 10 amino acids;

(b) reacting a terminal-$NH_2$ group of the backbone portion with a first t-boc and f-moc substituted amino acid;

(c) deprotecting the t-boc $NH_2$ residue;

(d) introducing an active peptide subunit onto the t-boc deprotected $NH_2$ residue;

(e) deprotecting the f-moc $NH_2$ residue;

(f) introducing backbone protein sequence onto the deprotected f-moc $NH_2$ residue;

(g) reacting a second t-boc and f-moc substituted amino acid and backbone terminal $NH_2$ residue;

(h) deprotecting the t-boc $NH_2$ residue of the second f-moc and t-boc substituted amino acid;

(h) introducing an active peptide subunit onto the deprotected t-boc $NH_2$ residue.

2. A peptide comprising: D-P-W-N-V-F-D-F-L-I-V-I-S-S-I-I-D-V-I-L-S-G.

3. A peptide comprising: A-R-T-V-F-G-V-T-T-V-L-T-M-T-T-L-S-T-S-A-R.

4. A peptide template comprising:

$$B'[(X)_nB']_m \text{ or } (X)_n[B'(X)_n]_m$$

where B' is a basic amino acid having a terminal amino group which is bound to a protective group, X is any arbitrary amino acid and m and n are integers from 1 to 10.

* * * * *